(12) United States Patent
Acland et al.

(10) Patent No.: US 7,462,455 B2
(45) Date of Patent: Dec. 9, 2008

(54) DIAGNOSTIC TEST FOR COLLIE EYE ANOMALY

(75) Inventors: Gregory M. Acland, Kennett Square, PA (US); Anna V. Kukekova, Ithaca, NY (US); Gustavo D. Aguirre, Philadelphia, PA (US); Elaine Ostrander, Potomac, MD (US); Dayna Akey, Seattle, WA (US); Orly Goldstein, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 68 days.

(21) Appl. No.: 11/255,019

(22) Filed: Oct. 20, 2005

(65) Prior Publication Data

US 2006/0115843 A1 Jun. 1, 2006

Related U.S. Application Data

(60) Provisional application No. 60/620,547, filed on Oct. 20, 2004.

(51) Int. Cl.
*C12Q 1/68* (2006.01)
*C12P 19/34* (2006.01)
*C07H 21/02* (2006.01)
*C07H 21/04* (2006.01)

(52) U.S. Cl. .......................... 435/6; 435/91.2; 536/23.5; 536/24.31; 536/24.33

(58) Field of Classification Search ....................... None
See application file for complete search history.

(56) References Cited

OTHER PUBLICATIONS

Lowe et al., Linkage Mapping of the Primary Disease Locus for Collie Eye Anomaly, Genomics 82 (2003) 86-95.

*Primary Examiner*—Carla Myers
(74) *Attorney, Agent, or Firm*—Hodgson Russ LLP

(57) ABSTRACT

The invention relates to a method for identifying dogs which are genetically normal, heterozygous for, or homozygous for the mutation primarily responsible for Collie eye anomaly (CEA). The method comprises the steps of obtaining a biological sample from a dog and testing DNA in the biological sample for the presence or absence of a 7.8 kilobase deletion within chromosome 37 in which the CEA mutation is located. No deletion is indicative of a normal dog. A deletion on one allele of chromosome 37 is indicative of a dog that is heterozygous for the CEA mutation. A deletion in both alleles of chromosome 37 are indicative of a dog that is homozygous for the CEA mutation. Also provided is a kit for identifying a dog as normal, heterozygous for, or homozygous for the CEA mutation.

14 Claims, 11 Drawing Sheets

```
   1 GTGTATTCAC ATCAACCAGC TTGTGGGCTT GTAGGTGGCC AAGGGAGGTC AGATCAGGTT
  61 GAGACAATTC CAGCGAATGG CCTGCCCTTC CACCTAAAGC CCTGGGATCT TTCCATATTT
 121 CTGTCCTTGT TTGTTTTTTG CGCTGCCCAC AGTACAAGGT AGGATTGTGA AGTAGGCCAG
 181 TTGCTCTCTC TGTGTTCTTC TTTCCTCTTC CTGTTTATTT TTCTTAAAGA TTTTATTTAT
 241 TTATTTATGA GAGGCACAGA GAGAGGCAGA GACATAGGCA GAGGAACAAG CAGGCTCCCC
 301 ATAGGGAGGG ACTCGATCCC AGGACCCGG GATCACCACC TGAGCTGAAG GCAGATGCTC
 361 AACCACTGAG CCACCTGGGT GCCCCTCTT CCTGCCTTTT TGTCTTCTCT TCATCTCCAC
 421 TGCGCTGTCT TCATGTTAGC CAGAGTTTTC CTTTACTGTT GAGGGGAGTC TGTTTCCTTG
 481 TTACACCCCG ACTCCATACA ACTCCTGCTG TCTTTTAGG AGCTGAACAA GCGCCTGACA
 541 GCTCCACCTG CGGCTTTTCT CTGTCATTTG GATGATCTGC TTCGCCCACT GTTGAAGGAC
 601 ACTACTTTCC CCAGCGAAGC TATGTTCACC TGTGATCATG TGGCCGAGGC ACTGATACTA
 661 CGGGTGCGGA GTGAACTCTC TGGTCTCCCC TTTTATTGGA ATTTCCACTG CATTCCTGCT
 721 AGCCCTTCCC TGGTGAGTGT AATTCAAGTG TGGAGTGGGG AAGGGGAATG CCAGCTGCTT
 781 CAAGATGAAT CTTTAGGTGT TCTTATTTTT GTGTGGATTC CACTTGAAAT TCTTCTTCAG
 841 TCAGAACACT TTCCTTGATT AGACAGAAGG CAAAACAGAT TCTCGACTGG TACATCTTTT
 901 CCTTGCAAAG GGAGCAGGGT TTGGGTTTAC CTGCTTTATT GAGCGTCTTT AATATTCAAC
 961 ATTTATTAAG CATCACTTTA GGCTGGTTGT TAGGTGTCCA GATCTAAAAC AAATAGCCTA
1021 TTCCTGGAGT TTATAATCTA GTGAGAAGAT AGACAGGAAG CAGAATAAAG TATGGTAAAT
1081 TCTTTGGTTG AAGTAAGCTC AGGATGAGTG AAAGTTTGAA AAACCTTTTT TTGAAGAGAG
1141 TTTTTTTTTT CCTTTAGAAA GTGGAGGGGG AGGGGAAGAG GGAGAGAGAG AGAGAGAGAG
1201 AGAAAGAGAG AGAGAGAATC CCAAGCAGGC ACCATGCCCA ACAGGAGCC CAACATGGGG
1261 CTCAATCTTA CAACCCTGAG ATCATGACCT GGGCCGAAAT CAAGAGTTGG GTGTTTCACC
1321 GACTGGGCCA CTGAGGCACC CCATTGAAGA GATAGTTTCT AAGTTGTGTT TTGGAGATGA
1381 GGAGGGGATA ACCGGGAGAA GATCAGGTCA GTCTAGGCTG GAGTGCATTT TGAGAGGCAG
1441 GGAGATGTAT AGGTATGGGG CAAGGGAGGG AATTTCATGA CTGCAGGAAG TTGTGGGAAA
1501 TGAGGTGGGC ATTTTGAAGA ATTCTAATGA GTTTGGATTT TATCCTTAAG GCAACAGAGA
1561 TTCATTGAAA AAGTTTATTT TATTATTAGA AAATATTTAA TTTATTTATT TGAGAGAGTA
1621 AGAGCCAGAG AGATCAGAGG GAGAGGGACA GGGAAAAGCA GGCTTGCTGC TGAACAGAGA
1681 TCCCAGTGTG GGGCTTGATC TCAGGACCCT GAGTCATGAC CTGAGCTGAA GGCAGACGCT
1741 TAACCGACTG AGCCACCCAG GTGCCTGCAT TGAAAAACTT TAAGCAGGGG TTTAACATGA
1801 TCCAGTTCAG ATCAGTCTGG CAAAGGATAG AGTACGTGCC AGTGTTAGCT ACCTTTCTGA
1861 ACATTTGTCA TTGGATCCTC ATGACTATCC TGCAAGATAA GTAGTATTTA TTCCTTGTTT
1921 TCAGAGTAGG AAGCCAAGAT TGAAGGCAAT GTGTCCAAAG TCATCTAACT TGTAAGTGAA
1981 TGAGCTGGAA TTTTACTCCC AGGGAGGTCT GATTCGAGAG CCTATTTTCA AGGACTAGGA
2041 TGATAATGTC TTCTGCTTAC ACAGCTTTCT AGGCTTCCAG AGCTTTTATT TTTTATTTTT
2101 TTAAAGATTT ATTTATTTAG TTATGATAGA CACACACACA CACACACACA CACACACACA
2161 CACACACACA CACAGAAGCA GAGACACAGG CAGAGGGAGA AGCAGGCTCC ATGCTGAAAG
2221 CCCGATGTGG GACTCGATCC CAGGACTCCA GGATCGTGCC CCGGGCCAAA GACAGGCGCC
2281 AAACCGCTGA GCCACCCAGG GATCCCTCCC AGAGCTTTTA TTAGAAATTA GTTTGACATG
2341 GGAGACACCT AACTCTGGGA AAGGGGTAGT GGAAAGGGAG GTGGGTGGGG GGTTGGGGTG
2401 ACTGGGTGAC GGGCACTGAG GAGGGCACTT GGCAGGATGA GCACTGGGTG TTATGCTAAA
2461 TGTTGACAAG TTGAACTCCA ATAAAAAAAA TTAAAAAAAA TTAGTTTGAG AGAGACGCTG
2521 GGGTGACTCA GTGGTTGAGC ATCTCCCTTC AGCTCAGGTC ATGATCCTGG GGTCCTGGA
2581 TCGAGTCCCA CATTGGCTTC CCCACAGGGA GCCTGTTTCT CCCTCTGCCT GTGTCTCTGC
2641 CTTTCTCTGT GTCTCTCATA AATAAATGAG TAAAATCTTT AAAAAAATAA ATTAGTTTGA
2701 GAGTAAACAG TAAGAACTTG TTTGCAAGAA TTACTGCCAC TGGTCCCTTC CACCCTTTTA
2761 TATAAACAGA GCTGTTTCAG TCAGTAGCAT TAGAGGCCAA GGTCTTCTAT GGGAGGCCTA
2821 AGGGTGTAGG TTTATCAGCA GAAGCACTTG AAGACAAGTG GGCATCATTT CCTATATCCT
2881 TTCTTTAGTT TTCCTGAGGT CATGTGATCT TTTGGCACCA ACGGAGTGGA TGGGACCAAG
2941 TATTTTTGAG AAACTGTTCT TTGGTGGATT TCTTTTCTTA AGATTTATTT ATTTATTTGA
3001 GAGAGAGAGA GTGTGTGTGT GTGTGGTTGG GAGGGACAGG GCGAGGGAGA GAGAGTCTCA
3061 AGCGACTCCA CGTTGAGCAC CGAGCCCAAT GCGGGGCTTG ATGCCATGAC CCTTAACTGA
3121 AACCAAGAGT CAGAGGCTCA ACTGACTGTA CCACCCAGGT GCCCCTCTGG TGGAGTTTTG
3181 ATTTGGAATC CAGTAAAGGT GGACTTGAGT GCTTGGAGAA CTTCTCATTC ATCTCTGAAT
3241 TTCTGAGGTC CATCAACAGT GTTTAGCAGA TAATAGTTTT GATCTGTTGA TTTTCGTGAA
3301 ATTTTTTGT GCAATTTTCC ATCCTTTAGA TAGTTTACCT CTGGTTCAAA TCCCTGTAAT
3361 TTTTTTCTAA GTAACACCAG GGGGCACTGT TCCCTCAATA ATGCTTGTTC TGGAACCAAA
```

Figure 1A

```
3421 AAAAAAAAAA AAAAAAAAAG TGTTCCGGGA GCCCTTGGGA AGTCCTAGCA ATAGCTAGTC
3481 TCATTGTGCA TCACACAGCC CTCGAAATTC AGAATAGTGA GATTGAGAAG GTAGTTCTAG
3541 GAGGGTGATG GGCTCTGATA GTTTTTTTCC CCCCAAATTA AAAGGAAACT TGTATAATGA
3601 TATTATACTA GAAAATAATA TGTAAAGGGA AAACGAGCTA TTCTAGGCAA ATTCCTCTAA
3661 TTGGGCAGCC CCAATAAGAA AAGAAGCTTC AGTATTGGGG AGACCATTGA ACAATTGGTG
3721 AACAATTAGG CTTTAAGGTA AAATAAAATA TGTATTATTA TAAAAAGAA GACTACCAGC
3781 CCAGGGAAAC CCCTGAGCCT GAGGAAGCTT TATAGGGAAA AAGTTAGAGC CAGCGGACAC
3841 TGTCAAGGAT GTAGGCGGAT ACTATTCCAG GCTTGTGTGT GTGTCTGTGA GGTCACACAG
3901 TCATAATTTT TGTTTATTAC TCATTCTTGT GATAGTTTTT ATTTCATTTT TTTTCAATGA
3961 GTAATTCATG CAAAAGGCAA ACATTTCAAA TAGCATTAAG AAAGGGTCTA GAGTGAAAAA
4021 ATAGGTCCTT CTACTCCACC CTCTAGTCTG TTATTTTCCT TCTTTAAAGC AACTACTGAT
4081 ACCATCTTCT TGTGACTTCT TAAGGAAAGC TATACGTAGG TTTGTGTAGA TGTAAGTATG
4141 TGTGTACTCA CACAATCAAA TACTTATCTG GGCGTATGGA TGCCTTTTCA CAAATGGCAG
4201 CATACTATCC ACACTATTCA GTAGCTTGCT CTTTTCACTT AATTATAGAA CTTAGAAAAT
4261 ATTTGTAACA ATCTGCTTGG ACAATCTGCT TTAATATTCT TTAATGGTAA CATAGAGTTT
4321 TATTTGATGG CATATATCAA CTTGTATTGA ATCGATACAC TACTAGTAGA TACTTAAGTT
4381 GTTTCCATTC TTTTGCTGTT ACACATAGTG GCTACTCTTG TATTTACTTT TCCTACGTGT
4441 AAATGTAAGA GTAACTTTCT AGCAATGGAA TAGTTGAATC AAGGAGTATT TGGGGGCTCC
4501 TGGATGGCTC GGTCGGAAGG GCGTGCAACT CTTGATCTCA GGGTCGTGAG TCTGAGCCCC
4561 ACATCAGGTG TAGAGATTGC TCAAAAAAT AAATAAACAA ATGTAAAAAA AAGGAGTATT
4621 TGTATCATTA ATATTGCTCA CAATAATGCC AGATTGTCTC TCAGAGAGCT TGCACACCTA
4681 AACTCCTACT AGCCATGCAG GAGAGTAAGA GAATACAGCG TGTGGTGTGT TCACGCCAAG
4741 ATCTCAAGGC TGTGCAGGAT ATCATGAAAT ATCTCAAGCC TCAGATTTCT GCTTTCTAGC
4801 CCATTTCCAC TTCCAGCCAG CTTCCTTCAT TCCTTCTTCC TCCTCAAAAA TGAAGGAGTC
4861 CAAGTATGTG CTCGCAATGA CTTATCCAAG GTAATAGAAA TCGAGTGGTG GAGCTGAGTT
4921 ACAAAGCAT GTGTGTTCTT CCTGCCACAC AAAAAACCCG TTGTATTACC TTGGATAAGT
4981 CATTGAATTT TTATGAGACT TGGCTTCATC ATTGATAAAG AGGAGGCACC AGTCCCAACC
5041 TTACTATGGA ATCCTGGGGA CTAAATACGA GAACATACAT AGTAGTACTT AGCTTCAGCA
5101 TTACTGTGGA CCTTTGAGAA CACATACTCG GACTCCCTAA TTTTTCCTTG AAGAAAATAA
5161 GGGCCGTGAG AGTGCTTGGG ATTAAGCCAT TTCACATCT AGATGCTCTC AGAGCCAGGG
5221 CTAGAATCCA GATGGAATTT CCAGTCTGTT GCTCTTGTCA CCATATCCAA ACCTGATAGG
5281 ATTCATTTTG GGATTGATAA CTGCCATTCA GCTCTCCTGC CTCTGACTGT CAACATTTCA
5341 ATGGGAAATC TGCAGATGTC AGGGGTGGGG GTGGGGGTGG GAGGGTGTTA TAAATAGATT
5401 TCCTCTGGAA AAGATTGACA ACTCCTGCTT CTGTATCTAC CACACTTCCT GACCTCCTTA
5461 ACTCTCCTGA GAAATTTGAG AGCAGAAGCC TCATGGGTTC ACAGCATGTA CTAGGCACAT
5521 AGTAGGTGTC TGTTGAATTG GCTTGTGGAA TCGCACCTCT TCATATATCA TCGTCTGCAA
5581 ACGAAGGGGT GGGGGTCTTC CTGACCTGAA GTGCTTCAAG ATTTTTCCTT GAAAATCCTT
5641 GAAGTATCTG TGGATTTGCT TTGAAATCTA TTACTTCAGC CACATGACTT GTCCTAATTA
5701 ATTGTCCTAA GCATGCATCT AACTTGGAAA TGAGTTATAC CCCAATGATT CAGAGTGGTG
5761 TAGTCCAATT CTATGAAATT ATTTGAAAAG TTGAGATATT TACTGAGAAA AAGCTAAATT
5821 ATTTTTTCTT TGTTGCTATA TAGACATTGG CGTCTGGTAC ATAGCTTCGG GTGCCTGGCA
5881 TGGCATTACT TTATTTATTT ATTTATTTAT TTATTTATTT ATTTATTTAT TATTATTTTT
5941 AATGATAGTC ATCACAGAGA GAGAGAGAGA GAGAGAGAGG CAGAGACACA GGCAGAGGGA
6001 GAAGCAGGCT CCATGCACCG GGGAGCCCGA CGTGGGACTC GACCCCGGGT CTCCAGGATC
6061 GCGCCCTGGG CCAAAGGCAG GCGTTAAACC TCTGCGCCAC CCAGGGATCC CTACCCTATA
6121 TATTTAGATA CAGCATTGAT TAAAAGCTGT TTCTCCTTAT GTTTCCTGTT TATTTACCAC
6181 CACTCAAAGA GATCGCTGTT AAGGTGGATT CCCAGAGAGA GGCTGGTTGT CACCTTTAGG
6241 AGTTTCTGTT ATTTGAGGGC TGCCGCCAGA GGGATGGTGA TGCTGCTTGG TTACCAATTG
6301 CAATTACTTT CAGTTCAGCC CCTCTAAACA CGGACTTGCT TTCATACAAG GATTCACCTA
6361 TTTTTCCACT ATTCACCTCG AACAGGACAA AACCTAACAA AATAGTTCCT AGGAAAGAAG
6421 GTTGGGTCTG GAGCAGATGA ATTTCCCCAA AGCAGAACTT CTGCTGCATT TTGAACAGTA
6481 TTTGGAGGCT TCAGTTTATC CTTAGGACCT GAACTGGGAA CCAGGACCAG GTTGGGATGT
6541 GCTGCATGAT GGGAAGAAGT GACTGGTGTT TCCAGCTCCA TTTGACTTCT GGCCTTCTGC
6601 TCTGCATCAG CCCCCCTGCA TTTATTGGGT CCTGGTGGTG GTACAAAAGC TGCTGCCTCT
6661 CGCCCGTATC CCCCTCACCC CAATCTCTTC TCTTCTGATC TGTCCTTAGA GAAGCGTAGG
6721 GGTGCCTATA ATATGGCCAG TTGGCCAACT CTGGCTTGCT GCCTATTTTT CTGAAGTTAT
6781 GTTGGAAACC CACTACCCTC ATTTATTACA TGTTGTCTAT GGGCATTTTC ATGAAGTAAC
```

Figure 1B

```
6841 AGCAGAGTTG AGTATTGTGA CAGGGGCTGT ATTGGCTGTA GAGCTGAAAA TATTGACTAT
6901 CTGACCCATG CAGAAAATGT TGCTGACCTC TGATCTCGGG CCTTTCTTTT TAATGTTTCC
6961 TTTAGCTCAT CTCCTTGGGG AATGTGAAGG AAACCTTGAT AGCATCCTTT GGTCACAAAG
7021 AAATTATTGA TTTTATTTAT TTATTTATTT TTAAAGATT GTATTTATTT ATTTATTTAT
7081 TTATTTATTT ATTTATTTAT TTATTTGACA CAGAGAGAGA GTACATGCAC AAGTAGGCAG
7141 AGCGGCAAGC AGAGGAGAGA GGGAGAAGCA GGCTCCCTGC TGAGTAGAGA GCCCAGTACG
7201 GGATCATGAC TCTCTGAGCC AAAGGCAAAG ACAGACTCTT AACTGACTGA GCCACACAGG
7261 TGCTCCGAGA TGATTGATTA TAGTTATTTT CTTTGGCTAA GGCTCTTTTC TTTCTAAGAC
7321 TACTGGATAC CTTGTGTAGG TGAATTAGGT AATTATTCTA TATAGGTATA TGTTGTTATA
7381 TGAGAACAGC ATCCTAGTTG CACAGCAGCA TGGCTATGCT TATGTCCTTC TTACCTTGTT
7441 AAGAGCAAGG TGTGCTGGGC CAGTTCATC CTTCCTAGGC TGACCTCTTG GTGACTGGCT
7501 GGCTTCTGTT CCGATGACCT TAGACTTTGC TGCATTTGTG GGAGCAGATC GAAACTCTCA
7561 TTCTGGACTA TCATCAGCCC TGAAATGGCT TGTAAGCAGT GGCTGGGTCT AATTTCCAAG
7621 GCTTTCTGCT CTCTGTTGAC TTTTGTCTTC TGTTATGTGC CAGCTAGCAC ACTCTTTTAA
7681 CTACACCTAC TTTCCTGAAG CCTACTTGGA TTTTCTGCTT TTGTTAGTCT CTGCAGGAGA
7741 GTTGGAACAA CACCTTTCTC TTATCAACTC TGTTACAACC TTCTCTTTAA ATCACCACTC
7801 TGGGCTGTCT ATCCATGTGT TCTCCTCTCT TCTTCCCACC CTTTTATCTA TGCTACAAAG
7861 AAAGCCCTCG AACTTCTTTC ACATACCTAT TTAGTTACTG TATTTTTATA GCCATGTAAA
7921 TGGATTGCTT GCTTATGAAA CTGTAAGTCC CTGTGAAAAC ATATATTTT CAGTATTTTT
7981 CTAGTTCCTA ATATAGTGTT CGGGAGTACT CTGTAACTGT CTGTTGGCTG ATTGATATCT
8041 CTTCCATGAA AGGTCTCCCA GCATTGGTT CGTCCTCTCA TGGGCATGAG TCTGGCCTTG
8101 CAGTGCCAAG TGAGGGAACT AGCAACCTTG CTTCGCATGA AAGATCTAGA GATCCAGGAC
8161 TACCAGGAGA GTGGGGCTGT GCTGAGTCGA GGTGAGAGGG CATTCTTTGG GGGTGTTGGG
8221 TGGGGACTGG TACAGGTGGC CAAAGGGCCT CAGAAAATGG GAGAGTCATT TGCATTAGAG
8281 GTGTGCTTCC CTGAGGAGGT GCTGGGTACT GACCATAACT GGAGACTTGA GGCTGGGTGA
8341 TACTTCTCTC TGCCTTGATG ACCCAGCTGG CATCCAAGTA GCCAAAAGAA ACTGTAGCTG
8401 AGTCCAGCCA TTGCCCCAGG CAATGGCAAG GAAAGAGTTT GGAAAGGGGC CAACAGTTGT
8461 GCAAAACTGT ACGAGGGCAG CACAAACATA GGGTGGGACC CTATGAAGCA TAGCTCCAGC
8521 TTCAGAATAA AAATTCAGTT CGACCTTCGT CTTTGTGGCG GGATGAACTC CTAGAGCACA
8581 TGCTGCCACT GAACACATCC TGTGTTGCTA ATCACCCTCT CCTCCTCCTC TGTTTGCTCA
8641 CACACTCATC CCTTCTCCCA CTGGACTCCG GGTGTTACAT GTTTATGCTC CCTACCAAGA
8701 AATCTTGGGC TCTGTTTCTT TTCCTTCTCA CAGGCAGAAA GCTCATCTTA AGACTAACAT
8761 TTCTTTTCTG TATTATTACA GATCGGTTGA AGACGGAGCC ATTTGAAGAA AATTCCTTCT
8821 TGGAACAATT TATGGTAGAG GTAGAGTATA CAACAATAAG GATTTTCTTT CTCCTTGTGC
8881 ACTTTTGCTT TATTTTCTTT CCAGGTGCCC GAGTAGTGAC TTGTGTTTTG GGTGCTAGCT
8941 GGTTTGCATG GTTGGAGAAT CCTTTCTCTG CAAAAGTTGC CTATAGAAAA TCTGTTAAAA
9001 CTTGAGATGC ATGTGGGGAA GATGGGGTGA AATAGGGGC AAGACTATGA AAGGCAAAAG
9061 TGGGCTGGTG AACATTTGTA AAAACATCTG TGCTAACGTA CCTAGGAGTT TCATTTAGAA
9121 TTCCCTAACC TTGGAGAGTT TGGTTGCCCA GTCGATCAAA TTTTTGCTTG TTGAGATCTG
9181 ATCACAGGTC TGGATTGTGG AGCAGGGTGG GGGGAGGAGT CATCATGACT TGCCCCTCCA
9241 ACATCCCACA GCAGAGGAAG GTGAAAAGCA CAGGGTTACC ATTTGGGAAC TGTCTTGTGG
9301 Gcacagtaat ctgtggaaaa tcacagtgtt tatacaaggg gactggcaaa ggaatgaatg
9361 gggagtagat aattgtggcc tgtcagaagc tcctgcctag gtttctcttc taaggattga
9421 gcttggccaa aagaaacatc tattaaacgg caaacagggg agtattaata atagtgacct
9481 ttgataaatac cagtcaatat tgattttctc ctctcactct tttaggactt gttggttgta
9541 cagttagtac cttcatctta ttgccctctt ttctaattat acacattaac caagctggta
9601 ctttactatg taagcaaata atgctattat aatattgtgt tctgtataga ttactcgtgt
9661 ttctgtcttg tcatctaggc tactttgtaa actcctggtg gacagggact atgactcata
9721 tttcttttga acatgaagtt agtattttc gcagggctag gcagaaagca ggtgtttttg
9781 acttggaacc ttctgttctg cctctgtgca gtggctgagc aaagacgcca tcgtgcttgg
9841 ggtcttaaca gtgagaacca aaaatgcaag ttgagtgctc aagcctatct cctgaagcaa
9901 tctaactctg gagaagaagg aaagcatgca ctgtgaagtc ctgaggcaga gtagatttca
9961 agtctttatg gggaaagaga gccccttaca cctggacttg cacagagatt tcctaggcca
10021 tttttctgtc ggagagcttc ctccgtctct aagtgtaggt tttaaggagg ttaatgcagg
10081 ctgaggatga tatgctgatt ccctgtctct gccccttagt taaataatac aagacttatt
10141 ctcagcccag cagagaggtc ccttcctgat ctggtgcctg cgtacctatc cagctgggtt
10201 tcttgagatt tttctttata aaccttaggc ttcagtcaga gaatggcttt gaattgccaa
```

Figure 1C

```
10261 aatgccttcc tctcgccttt atgtcttggc acacattgtt tcctttatct ataatgccca
10321 atgccctggc cttatctacc ttgtaaactt ctattaatct tttaagtgtc agctttggct
10381 tctttgagag acctttccag actctccttg taaagataat ccttcttccc tgctgctata
10441 gtaccttggt tcctacctcc gttttatcac atagaacttt gtgatattac tgtctatagg
10501 tcttcaagac aatgcctttc tcctctgttg atctctgaaa accatctgag ggcaaggact
10561 gcgttgcatg catttctata tccccggggc ctgaacatag tgcctgggag tagtagattc
10621 tctgtaagtt tgtgggtgaa gatgttacta attttgtgct aggggagtc tcatgaaaat
10681 tggggcagtg tggcctgtgg atatggtgct gctgtgagac ctaagtttgg ggtcttcagt
10741 tattctcctg ctttattttg cagctttgga taaattagta cttccagaga ctctgttttc
10801 ttatttgcaa aattggaggc tcacctcttc catgcttttg gggtaggggc aaccctgcag
10861 agtcgaatga gaaagcatag aatcctggtg ccagcccggg gaagagtatt actgcattgg
10921 aaccaattac caattacttc agaaatactg gtctcttaag tcctgggtgg atcacaccca
10981 aaccacatag acgtacagaa ttttacatat ctgcagagga tctgagagac aagtagctat
11041 agctttccat ttcacagact aagaaattgg gcctcagaga ggttaagtga cttacctaag
11101 gtcatgtcgc tgtagctgta tgtttagagc cttcctacat ttcttgtctg gatcatctc
11161 tattttgttt tgccactcta actggttgta cacaccaatt aaaggatggt taagggctag
11221 gatcatgggg aattattgtg acctctggga tcactgcatc gtcctctggg atcaccaaat
11281 gttctgcata gctgctagaa cccatttct aatgggactg cagaatttct tatggccatt
11341 gcatcttttc agttactctg cttgtctggg gtcctacaaa caggacacag aagggtcatg
11401 gggtcaccta aaacagctga aaggatgtgc atcaaaata agcaacatag aagataaac
11461 aaaccaggga cagagagctc ggggtgaagg tgcaggggggg ccagggctga tgtcagaggg
11521 ccacgcggtc agtgcctggg gtctgttttt cctggttcta ggcgagaggc tggagagata
11581 gggcacagag ggcagtagga cagggaggtt tctaggatac taaggccagg aaaaatattt
11641 aagggttgaa cagaggttac atcttcatat ttagttcttt tgttttcct ccctaccc
11701 ccgctttgag ccttggattt ctcatttcca gggagcccaa ggggccagt tgatggtggc
11761 ccgactggag ggggagtgct ggcagtgttc ttcaagtcga ctggacgggg tggcttcagg
11821 catgattttc atagagggaa gatcctcgta gagagcatct cctaggactg ggagctggga
11881 ggcaccgtta ggagtaggag atgagtcaac gaatcaggga ccattactgc aaggcagtag
11941 gaaccgtgtg aaagaagttt aggaggatca ggctggcatg gccttctctc actctggtcc
12001 actggaggga gttccttctc ccggccccat ccatgcctcc tcctctccat ctggttgcca
12061 tcaggctgtg tggctgctgg cgggctcttt atttatttat cccagtgtaa tggggtgagg
12121 agggagctgg cctgaggctg gcattccgag gccatgccac tgagccacag gcggtttgca
12181 tgggtgtgtg agtcactggg gctgcatgct gctcaaacca gacgcggcca ggctcaggga
12241 cagcaggcag cccaaaatag agccccgccc tctgcagctg caacccctg gccaggaatc
12301 agcccttgac accaaaacct gagcaattgc atgaagttgg cttctttcag tgagggtggg
12361 ggtgggggggg gcacttgaca gagagatcct ctccttccct gtcttcagag gagtgtattc
12421 agcacaatag tccttcccac tgatgcatgc cttatacgat ttaaattaat ctgttcaatc
12481 caataccttc agcagtttct atcatatact tatatgacta tagtgacatt gatttgactc
12541 agcatcctaa atgtagccac agcctttgtg tcctgtctag ttttagtact gtcttcattc
12601 cctgtctggt tgcagcctgt tgctagagca gatgcttcaa gttgtgacga tattcattgc
12661 tgctcttaga aagctggaag ttatatcaaa gccgccctgg gaagaggagg aggagtcctt
12721 gaacctggaa attgcttgct gtccagttga gttcattcac ggacagcttc tgcttggttt
12781 ccttggctgg cgttccattc tttacctgct ccttaaatgt tagtgttaat tcaaaattgt
12841 gtcctcatcc acttgtcctt ctctctctgg gtcatctcat ccagacccca atttgaactg
12901 tcactattat accaccaagt gccaattta tatctcccat catgcagccc atatttcttt
12961 ctgcacattt gatgtttcta cctggatgcg tcccacattg tactaccta aacatgtcca
13021 aaataagcca cccactcccc ctctttctct tctgatattc ctaatcttgg agaatcctac
13081 ccgtatccat tcagctttct aagccagaaa cttgggagtt actcactttt ctctttgtcc
13141 ttactttcaa atcctacttg tcaactatct tttgaatctg ctcctctcta atctggtgtc
13201 tgttgcctta gaatagcagc acccacccga ctcacccac aattgaattt gtattatgtc
13261 agagtgatct ctttgagaca gaaacagaaa tccagttgct taaagccatt tagtggttca
13321 aactccttgc atggcacaca gggtcgttca tgatttggtc ctcttgacct ctacagcttg
13381 atcctctgcc actttcccaa attgaagtcc tgatgcttat ttattccttg accagtgtgc
13441 ctgggattct cttcttct gtcctcacgg cagactcctg ttcagctttc ctgactgcac
13501 agacatcatc cctttttgtga gctttccatg accatttctc ctttccttgg tctgtttcc
13561 ttgccggcac aggtacactc tcctgctgtt cccgccgcct cctgtactga ctgacctctc
13621 ccatagcatt tggaggacat ggaacgaaca ggatatggga atgaaaagga aggatgggga
```

Figure 1D

```
13681 ggcaaggaaa attgagttgg ctgatctttt ctcatttaga ttttccttt agaagacttg
13741 ttaattcctt ctcctcaatg ttttcttgat atggcttcca tactgcaaca ctctcctgtt
13801 tttcttccta cttcatcggt tgctccttt cagaatctcc tgctggttct ttctctccct
13861 tacctctttt ttttttttt ttaagatttt atttatttat tcatgagaga cacagagaga
13921 ggcagcgaca caggcagagg gggaagcatc tccatgcagg gagcccgatg tgggacccga
13981 tcccagtctc caggatcaca ccctgagcca aaggcaggca ctcaaccatt gagccaccca
14041 ggtgtccccc tactttttt taaagtaatc tgtacaccta acgcagggct gaactcacaa
14101 cgctaacacc ccaagatcaa gaatcgcata ctcctctgac tgagccagcc aggtgtctgt
14161 cccttacctc ttaatgttgg ggtgcctcag gattcaatca ttggtgctct tttttaactt
14221 tagtgatctc atatagtccc atggctttaa ctaccacttt attgacaaat cccaaattta
14281 atctctaccc ttagaccttaa cctccaaact ctagactgtc tgcttgatat tcccatgtgg
14341 aagtccaaca gaatctgaaa ctctacatgt ccaaaactga acttctaacc ttaccccag
14401 atttgttttt ctaacaacct ccttccatct tagctgatgg aaatgtcacc ttttcatttg
14461 ctagggccac aaaccttaga gtcatccttg acttctgtct ttttctcata tcccacatct
14521 agtccatcag gaagtcctgt tggccttcaa aacacaccca taatttcacc tttgctgctg
14581 ccactctggt ctgagccaca attgtctctt tcttgcatca ttgcaataac ctctttattg
14641 gtgtctctgc tgctacctat gccccttc ggcccattac cagcaaagtg atcttattaa
14701 aatacagatc acatcatgat actccctgc tcaaagtcct tcattagttt acattacact
14761 tctagagtaa aacctaaagg cctttacagt ggcctacaaa gccctacgtg atctggacct
14821 cattaccttt ctgatttcat ctaccacttt ctccttcctt tactccattg cacccacact
14881 ggccgcttgc tgttttcta gcactttcta gcaccacttg cctttagtcc tttatgctgc
14941 ccatttcctc tgcttggaat gctctttctt cagatatttg tgtggccaag tccttcactt
15001 cctttatgtc tggattagtt atctatcgct ttataacaca tcattccaaa atgtcatggt
15061 ttaaaacaac aaacagttgt ggaaggtcag gaatttggaa gcagcttagc tgggtgattc
15121 tgattcaggg tctctcatga agtcacagtc aagatgttgg ctgggaatgt gattattctg
15181 aggcactgga gaattcactt ccaagttctc tcatgtggct gttggcagga gatgctgttg
15241 ccctgtaaca tgacctctcc atggggtttc ttacatgaca tggccctgcc ttcctcaga
15301 gcaagtgatc caaaagacag gcgaagactg aaatggaagc tgcagccttt ttataaccta
15361 atctcaggag tgacagcaca tcactctctt gtggtgatct cttcattagt agtgaagcag
15421 taaatgtagg ccacattcaa ggggagggta actaagctcc acctcttaag gggaggtgtg
15481 tcaaaaatac aatacatggt tttgttcaaa tgttaccttc acaatggagt ttactgtgag
15541 tatcctattt aaaatcataa gccacatcct cgcctctctg cacatgactc taatttgat
15601 tttttctata gcattcatct tccaacatac tataaaattt ccttatttca ttatgctcat
15661 tgttcatggc atcttccccc tgttagagct tgtaagctga gcaaggacaa ggatggatgt
15721 tttgtgccct ggttcatcca gagtacgtag aacactgcct ctacacacag taggcactca
15781 gtacatattt gttgaatgga tgaaggaatc ttagcttccc actcttcttt attttcccta
15841 tcttatgaat aggccatgaa atgatcaccc tgttggtagt ctgagaccta gatagcccta
15901 ctataaatag atgagtaacc taaggagaga attgctgtca gattgccatt cattctccca
15961 cctgcctgtt tactgggata taatcccaat tttgggatga actataaacc ttgaatcttt
16021 tattactgaa atcccctaaa acctctcttt tagacccagt tcagaaagca actatctggg
16081 atccctgggt ggcgcagcgg tttggcgcct gcctttggcc cagggcgcga tcctggagac
16141 ccgggatcga atcccatatc gggctcccga tgcatggagc ctgcttctcc ctctgcctgt
16201 gtctctgcct ctctctctct ctctgtgact atcataagta aataaataaa aattaaaaaa
16261 aaaaaaaaaa aaagaaagca actatctcag aaaccaaaag aataagaacc taccagggca
16321 cctgggtggc tcagtcggtt aagtgtctgc ctttggctca ggtcatgatc tcagggtcct
16381 gggattgagc cccacatcag gctccctgct caacggggag tctgcttctc tctctccctc
16441 tgcccctcc ccccgtgctt gtgcgggtgc tctttctttc tctctgtctc tctctcaaat
16501 gaataaataa aatcttaaaa aaagaaaaag aacctaccaa aatcctggaa agaacattag
16561 tcatacagcc aaaagcaagt taattagttt cctctttcct cagttttcc tctccctgag
16621 ctgccctgcc accataagcc cgttattcaa tatgtagagg aagacacagg actcagcata
16681 ggtatttca gtatcccat ggcatcatg aagcaggata atctagggg catgagactg
16741 tcctccgtac catcgtgtgt gtcagtactc tgatctagag aaacttacag ttaattcatt
16801 cttccggtag tcagcatggt gcatgttctt gtgggcata cggggatga taatattatc
16861 atcaaagagc tcgctgtgct taatgaatga taatagggggc tacaatagtg tagtgattgg
16921 aaaaagcttc ctgcaaaagg caggacttga tctggacttc tgtgtttgtt tggggttttg
16981 ctagggaact aggtggaagg catttagct gggaagcaca tgggcaaagg atgtaaagtc
17041 ataatgagtg ggtgaggatt agcagaaaat aaggttagca agatgataac tcgaggccag
```

Figure 1E

```
17101 gTTGTTGGGG AGCCTTAAAT GCTGGGCTGG ATGATTGGTA CTTTATTCTG AAGGTAAATG
17161 TATTTCAGCT TTTTTTTTTT CTGCCAGTAA TCCATTTATT TGCCTGTTTC AATCCAGTTA
17221 TTAACATCTA TCATTACACG CAGTGATTCT CAAACAGGCA CATTTCCCTA GGAAGGAGAT
17281 GGGCACTTCC TTCTCGCAGT TATTAATTAC TGTTATAGAT AGTGGGAAGC CGTGGAAAGT
17341 TTTGGCTGGA GAACTGACAT ATGAAAGCGA TCTTTGGCAA GATTAGGCTG TCAGTGGTAT
17401 GCCTATGTGA GCTGAAGAAT AGTGGTGCTA TTGACAGACT AGGAAAATCA TGGGTGGGGC
17461 TCAATTAAAT CTAATCTTGG GTATACAAAG GAATGGTTTT CCTTATTTAA AACACAAATC
17521 CACCAGTATT TGAGCTCTGG AATGAAAATC TCCAGGGAGG AAGGGATGGC TGCATATGTT
17581 TCTCAGCTAT ATTTCTCGGG AATTTTGCCT CCTCTTTGGG GTTTTCTCAA TGTGGTTCCT
17641 GTAGTCACCA TTGAGCCCTG CTACCAGGGG TCACCACCTC TTTTCTTTTT GGCCCCAGAA
17701 TATATTAAAA GGCTTCTTTC TTTATATTCC TTTTATAAAA CGTTATAGGG GCTTATGCTT
17761 TCAAAAGAAA ATTTATAAAA AATCTGAGGG CAAACAAAAA GGAAATCAGG ATGAAAATTC
17821 AAATGGGATA AAATTACTGA TATCCAAGAG ATGGATTTCT GATGCTGGGA ATCCTTAATA
17881 GTGGAGATCT TCATTAACTT CTGAATTCTC GTATCCTAAA AGCCTCAAAA TCAAGTGTTT
17941 ACTAACTCAA ATGTCTAAAG GGGACAGACA TACAATATAA ATATGATATC TTATATCAGG
18001 CTGGATATAA TACAACATGT TTTTGGGGGT CTGTGGAAAA CTGAATCGCA CATGCCCCCC
18061 TCTATCTAGA CCCAAATAGG TTAGCACAGT TGAACAGACA CTGTTCTGGG GGCTTGTGTA
18121 GTTTACTTCA CTGAAAGGAA GTACCAGCTC CTTCTAAAAT
```

Figure 1F

GACTGGTATTATCAAAGGTCACTATTATTAATACTCCCCTGTTTGCCGTTTAATAGATGT
TTCTTTTGGCCAAGCTCAATCCTTAGAAGAGAAACCTAGGCAGGAGCTTCTGACAGGCCA
CAATTATCTACTCCCCATTCATTCCTTTGCCAGTCCCCTTGTATAAACACTGTGATTTTC
CACAGATTACTGTGCCCACAAGACAGTTCCCAAATGGTAACCCTGTGCTTTTCACCTTCC
TCTGCTGTGGGATGTTGGAGGGGCAAGTCATGATGACTCCTCC

Figure 3A

GGAGGAGTCATCATGACTTGCCCCTCCAACATCCCACAGCAGAGGAAGGTGAAAAGCACA
GGGTTACCATTTGGGAACTGTCTTGTGG GC ACAGTAATCTGTGGAAAATCACAGTGTTTA
TACAAGGGGACTGGCAAAGGAATGAATGGGGAGTAGATAATTGTGGCCTGTCAGAAGCTC
CTGCCTAGGTTTCTCTTCTAAGGATTGAGCTTGGCCAAAAGAAACATCTATTAAACGGCA
AACAGGGGAGTATTAATAATAGTGACCTTTGATAATACCAGTC

Figure 3B

CTAGTCTGTCAATAGCACCACTATTCTTCAGCTCACATAGGCATACCACTGACAGCCTAA
TCTTGCCAAAGATCGCTTTCATATGTCAGTTCTCCAGCCAAAACTTTCCACGGCTTCCCA
CTATCTATAACAGTAATTAATAACTGCGAGAAGGAAGTGCCCATCTCCTTCCTAGGAAAT
GTGCCTGTTTGAGAATCACTGCGTGTAATGATAGATGTTAATAACTGGATTGAAACAGGC
AAATAAATGGATTACTGGCAGAAAAAAAAAAAGCTGAAATACATTTACCTTCAGAATAAA
GTACCAATCATCCAGCCCAGCATTTAAGGCTCCCCAACAACCTGGCCTCGAGTTATCATC
TTGCTAACCTTATTTTCTGCTAATCCTCACCCACTCATTATGACTTTACATCCTTTGCCC
ATGTGCTTCCCAGCTAAAATGCCTTCCACCTAGTTCCCTAGCAAAACCCCAAACAAACAC
AGAAGTCCAGATCAAGTCCTGCCTTTTGCAGGAAGCTTTTTCCAATCACTACACTATTGT
AGCCCCTATTATCATTCATTAAGCACAGCGAGCTCTTTGATGATAATATTATCATCCCCC
GTATGCCCACAAGAACATGCACCATGCTGACTACCGGAAGAATGAATTAACTGTAAGTTT
CTCTAGATCAGAGTACTGACACACACGATGGTACGGAGGACA

Figure 4A

TGTCCTCCGTACCATCGTGTGTGTCAGTACTCTGATCTAGAGAAACTTACAGTTAATTCA
TTCTTCCGGTAGTCAGCATGGTGCATGTTCTTGTGGGCATACGGGGATGATAATATTAT
CATCAAAGAGCTCGCTGTGCTTAATGAATGATAATAGGGGCTACAATAGTGTAGTGATTG
GAAAAGCTTCCTGCAAAAGGCAGGACTTGATCTGGACTTCTGTGTTTGTTTGGGGTTTT
GCTAGGGAACTAGGTGGAAGGCATTTTAGCTGGGAAGCACATGGGCAAAGGATGTAAAGT
CATAATGAGTGGGTGAGGATTAGCAGAAAATAAGGTTAGCAAGATGATAACTCGAGGCCA
G GT TGTTGGGGAGCCTTAAATGCTGGGCTGGATGATTGGTACTTTATTCTGAAGGTAAAT
GTATTTCAGCTTTTTTTTTTCTGCCAGTAATCCATTTATTTGCCTGTTTCAATCCAGTT
ATTAACATCTATCATTACACGCAGTGATTCTCAAACAGGCACATTTCCTAGGAAGGAGAT
GGGCACTTCCTTCTCGCAGTTATTAATTACTGTTATAGATAGTGGGAAGCCGTGGAAAGT
TTTGGCTGGAGAACTGACATATGAAAGCGATCTTTGGCAAGATTAGGCTGTCAGTGGTAT
GCCTATGTGAGCTGAAGAATAGTGGTGCTATTGACAGACTAG

Figure 4B

GGAGGAGTCATCATGACTTGCCCCTCCAACATCCCACAGCAGAGGAAGGTGAAAAGCACAGG
GTTACCATTTGGGAACTGTCTTGTGG[GT]TGTTGGGGAGCCTTAAATGCTGGGCTGGATGATT
GGTACTTTATTCTGAAGGTAAATGTATTTCAGCTTTTTTTTTTCTGCCAGTAATCCATTTA
TTTGCCTGTTTCAATCCAGTTATTAACATCTATCATTACACGCAGTGATTCTCAAACAGGCA
CATTTCCCTAGGAAGGAGATGGGCACTTCCTTCTCGCAGTTATTAATTACTGTTATAGATAG
TGGGAAGCCGTGGAAAGTTTTGGCTGGAGAACTGACATATGAAAGCGATCTTTGGCAAGATT
AGGCTGTCAGTGGTATGCCTATGTGAGCTGAAGAA<u>TAGTGGTGCTATTGACAGACTAG</u>

Figure 6

DIAGNOSTIC TEST FOR COLLIE EYE ANOMALY

This application claims priority to U.S. provisional application Ser. No. 60/620,547, filed Oct. 20, 2004, the disclosure of which is incorporated herein by reference.

This work was supported by grant numbers EY-06855 from the National Eye Institute/National Institutes of Health and R21 MH069688-01 from the National Institute of Mental Health/National Institutes of Health. The Government has certain rights in the invention.

FIELD OF THE INVENTION

The present invention relates generally to a hereditary ocular disorder, Collie Eye Anomaly (CEA), which affects development of the choroid and sclera in canines. More particularly, the invention relates to a method for identifying dogs as genetically normal, heterozygous for or homozygous for the CEA disease allele.

BACKGROUND OF THE INVENTION

Collie Eye Anomaly (CEA) is a canine hereditary ocular disorder affecting development of the choroid and sclera. The disease segregates in several dog breeds including Rough and Smooth Collies, Border Collies, Australian Shepherds, Lancashire Heelers, and Shetland Sheepdogs. The clinical phenotype varies significantly among affected dogs of all breeds. The primary CEA phenotype, choroidal hypoplasia (CH), is characterized by regional hypoplasia (underdevelopment) of the choroid, which is the highly vascularized bed of the eye that underlies the retina. This lesion usually results in an ophthalmoscopically detectable window defect in the ocular findus located temporal to the optic nerve.

In the most mildly affected dogs, CH is the only lesion apparent, and many such dogs will exhibit no obvious clinical consequences and retain apparently normal vision throughout life. In severely affected dogs, there may also be colobomatous lesions of the optic nerve head and or adjacent tissues. Colobomas are outpouchings of the eye wall, where there is localized thinness of the sclera. In the most severe cases, localized or complete retinal detachments, and/or intraocular neovascularization and hemmorrhage can develop, all of which can lead to blindness. These severe manifestations of CEA are only seen in dogs also affected with the primary choroidal hypoplastic lesion.

It has been previously established (Lowe J K, et al. Genomics 2003 Jul; 82(1):86-95) that the primary CEA phenotype is inherited via a gene that maps to a 3.9-cM region of canine chromosome 37, and segregates as an autosomal recessive trait with nearly 100% penetrance. However, because there has been no identification of an alteration of the gene associated with CEA, screening for the disease has not been possible. Thus, there has been an ongoing need in the canine breeding industry for a genetic test that permits direct identification of dogs that are normal, carriers or affected with CEA.

SUMMARY OF THE INVENTION

The present invention provides a method for identifying dogs which are genetically normal, heterozygous for or homozygous for the CEA disease allele. The method comprises the steps of obtaining a biological sample comprising genomic DNA from the dog and testing the biological sample for the presence or absence of a deletion of nucleotides corresponding to nucleotides from position 9,302 to position 17,101 of SEQ ID NO:1 within chromosome 37. The presence of the deletion in both alleles is indicative of a dog that is homozygous for the CEA disease allele. The presence of the deletion in only one allele is indicative of a dog that is heterozygous for the CEA disease allele, and the absence of the deletion in both alleles is indicative of a dog that is normal for CEA. The presence or absence of the deletion may be tested by amplification of the DNA followed by analysis of the amplification products.

The present invention also provides kits for diagnosis of a dog as normal, heterozygous for, or homozygous for the CEA disease allele. Such tools and/or kits assist breeders to identify normal dogs, carriers and homozygous mutant dogs. The dogs that are determined to be heterozygous for or homozygous for the disease allele can be eliminated from a breeding stock or bred with genetically normal dogs.

BRIEF DESCRIPTION OF THE DRAWINGS

FIG. 1 provides the sequence of SEQ ID NO:1 which corresponds to a region of chromosome 37 in dogs. SEQ ID NO:1 is a contig (a consensus sequence derived from multiple overlapping sequences) from nonaffected dogs. The area deleted in affected dogs and on one chromosome in dogs that are heterozygous for the CEA allele corresponds to nucleotides 9,302 to 17,101 of SEQ ID NO:1, which are indicated in lowercase. SEQ ID NO: 1 corresponds to nucleotides 28,676,370 to 28,694,530, (inclusive, size 18,161 bp) of the public domain assembled canine genome sequence, July, 2004 Assembly, which can be accessed through GenBank or at the UCSC Genome Bioinformatics Site at http://genome.ucsc.edu/. SEQ ID NO:1 corresponds to nucleotides 72,769-90,929 of the Defined Collie Eye Anomaly Linkage Disequilibrium Interval. The Defined Collie Eye Anomaly Linkage Disequilibrium Interval corresponds to nucleotides 28,603,601 to 28,716,392 (inclusive, size 112,792 bp) of the public domain assembled canine genome sequence, July, 2004 Assembly. PCR primer binding sites are bolded and correspond to the primer names and positions listed in Tables 3-5. Sequences in lower case identify nucleotides deleted in the mutant allele; upper case identifies bases present in both normal and mutant.

FIG. 3A provides the nucleotide sequence (SEQ ID NO:10) corresponding to one strand of the amplification product obtained using primer CEAF21a and primer CEAR17d. The sequence corresponding to CEAF21a is bolded; the sequence corresponding to primer CEAR17d is underlined.

FIG. 3B provides the nucleotide sequence (SEQ ID NO:11) of the reverse complement of SEQ ID NO:10. The sequence corresponding to primer CEAF21a is bolded; the sequence corresponding to primer CEAR17d is underlined. The boxed pair of nucleotides "GC" flank the start breakpoint of the CEA deletion.

FIG. 4A provides the nucleotide sequence (SEQ ID NO:12) corresponding one strand of the amplification product obtained using primers CEAF22a and primer CEAR22c.

The nucleotide sequence corresponding to primer CEAF22a is bolded; the sequence corresponding to primer CEAR22c is underlined.

FIG. 4B provides the nucleotide sequence (SEQ ID NO:13) of the reverse complement of SEQ ID NO:12. The nucleotide sequence corresponding to primer CEAF22a is bolded; the nucleotide sequence corresponding to primer CEAR22c is underlined. The boxed pair of nucleotides "GT" flank the end breakpoint of the CEA deletion.

Figure 5:
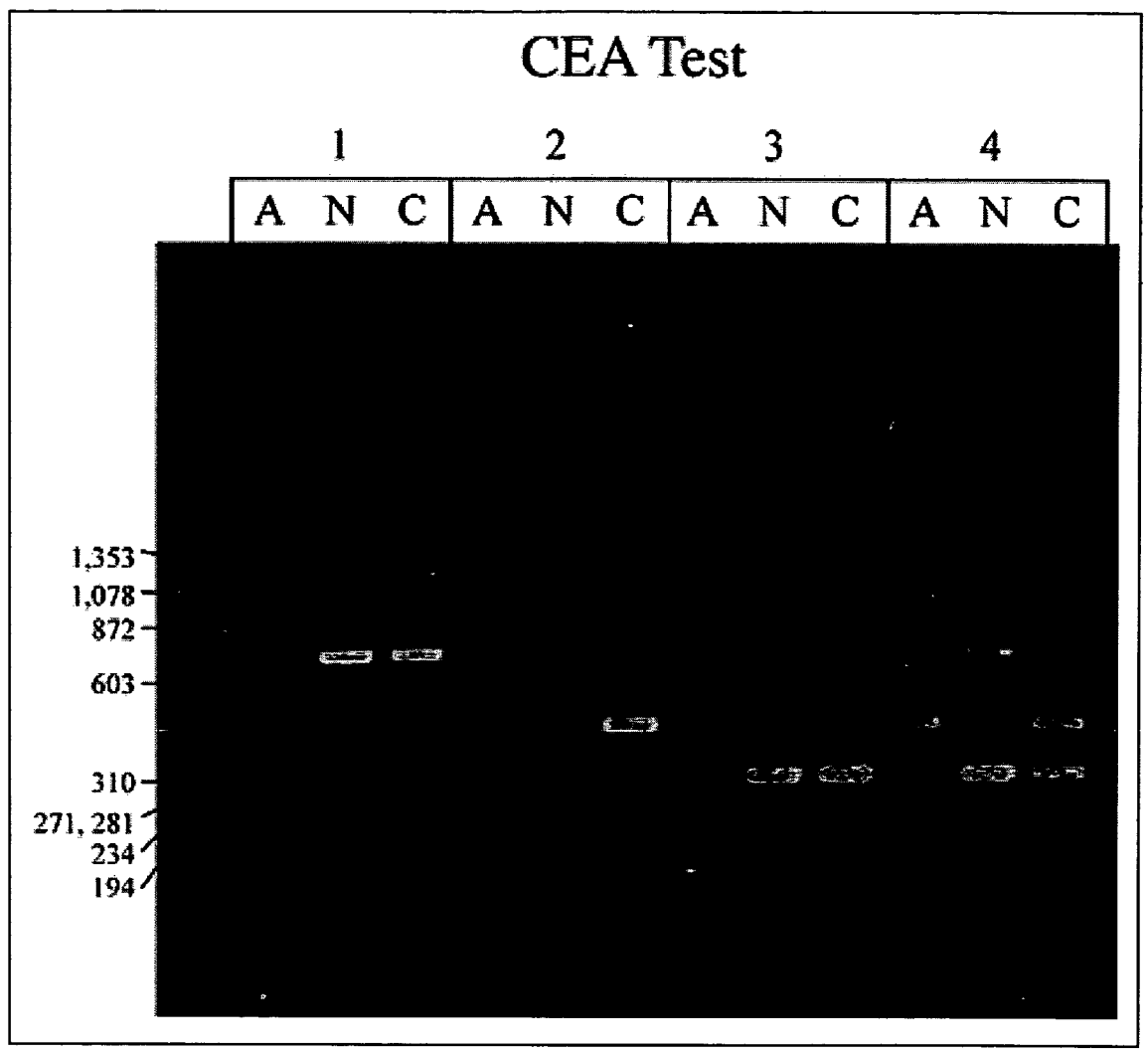

FIG. 5 is a representation of an electrophoretic separation of PCR amplification products obtained using sets of the four PCR primers disclosed in Table 6. The first, leftmost, lane contains a size ladder. The remaining lanes are divided into four sets of PCR amplifications (1-4) of genomic DNA from normal (N), carrier (C) and affected (A) dogs. Set 1 was performed using primers CEAF22a and CEAR22c. Set 2 was performed using primers CEAF21a and CEAR22c. Set 3 was performed using primers CEAF21a and CEAR17d. Set 4 was performed using a combination of all four primers.

FIG. 6 provides the nucleotide sequence (SEQ ID NO:14) of one strand of the 430 bp product generated by PCR using primers CEAF21a and CEAR22c. The sequence corresponding to primer CEAF21a is bolded. The sequence corresponding to primer CEAT22c is underlined. The boxed nucleotides "GT" flank the deletion site.

DESCRIPTION OF THE INVENTION

The present invention is based on identification of the mutation associated with the CEA disease. We have reduced the critical region in which the CEA gene is located to an approximately 100 kb interval on chromosome 37 by using linkage disequilibrium mapping. Within this interval, a 7.8 kilobase ("kb") deletion associated with dogs that are heterozygous for the deletion (carriers), or are homozygous for the deletion (likely to be affected with CEA), was identified. This 7.8 kb region is referred to herein as the "the CEA deletion." Without intending to be bound by any particular theory, it is believed the CEA deletion results in removal or disruption of a putative enhancer element related to the expression of the CEA gene.

Disclosed in FIG. 1 is SEQ ID NO:1 which was assembled from data retrieved from The Institue for Genomic Research (TIGR) database of the preassembled 1.5× survey sequence database of the canine genome, together with sequences amplified and sequenced in the laboratory of Elaine Ostrander, by Dayna Akey. The contig created from this data formed the consensus sequence for SEQ: ID NO:1.

In more detail, SEQ ID NO:1 was assembled as a continuous 5' to 3' sequence in the direction of transcription of the putative gene FLJ12610 as part of an effort to identify the entire genomic sequence of this gene. The portion of FLJ12610 represented by SEQ ID NO:1 is presented in Table 1, with introns and exons also identified.

TABLE 1

| | |
|---|---|
| 1-519 | End of Intron 1 of FLJ12610 |
| 520-732 | Exon 2 of FLJ12610 |
| 733-8,053 | Intron 3 of FLJ12610 |
| 8,054-8,191 | Exon 3 of FLJ12610 |
| 8,192-8,781 | Intron 3 of FLJ12610 |
| 8,782-8,840 | Exon 4 of FLJ12610 |
| 8,841-18,160 | Beginning of Intron 4 of FLJ12610 |
| 9,302-17,101 | sequence deleted in CEA mutant allele |

The gene FLJ12610 is transcribed from the reverse strand of canine chromosome 37, as it also is on the homologous human chromosome (HSA2). Thus, SEQ ID NO:1 runs forward in the same direction as the gene FLJ12610 is transcribed, but backwards in the canine genome assembly.

Table 2 shows the genomic positions of the Collie Eye Anomaly Linkage Disequilibrium Area, SEQ ID NO:1, and the Collie Eye Anomaly deletion. Nucleotide number 1 in SEQ ID NO:1 is the reverse complement of nucleotide 28,694,530 in the canine genome sequence, and the last nucleotide of SEQ ID NO:1 corresponds to the reverse complement of nucleotide 28,676,370 in the canine genome sequence. That is, SEQ ID NO:1 is the reverse complement of the interval 28,694,530 to 28,676,370 in the canine genome sequence.

TABLE 2

| Feature | Position on Canine Chromosome 37 |
|---|---|
| Start LD | 28,603,601 |
| End SEQ ID NO:1 | 28,676,370 |
| End CEA Del | 28,677,428 |
| Start CEA Del | 28,685,226 |
| Start SEQ ID NO:1 | 28,694,530 |
| End LD | 28,716,392 |

The breakpoints of the CEA deletion have also been identified. The CEA deleted region begins at nucleotide 9,302 of SEQ ID NO:1 which corresponds to nucleotide 28,677,428 of canine chromosome 37 of the public domain assembled canine genome sequence, July 2004 Assembly. Therefore the start breakpoint of the deletion (also referred to herein as the 5' breakpoint) is between nucleotides 9,301 and 9,302 of SEQ ID NO:1. The deleted region ends at nucleotide 17,101 of SEQ ID NO:1 and therefore the end breakpoint of the deletion (also referred to herein as the 3' breakpoint) is between nucleotides 17,101 and 17,102 of SEQ ID NO:1. When the CEA region is deleted, in a 5' to 3' sequence of the region corresponding to SEQ ID NO:1, nucleotide 9,301 (G) is followed by nucleotide 17,102 (T).

Based on the above observations, tests for detecting the presence or absence of the CEA deletion are provided. Dogs without the CEA deletion in either allele are referred to as normal for CEA. Dogs with the CEA deletion on only one allele are referred to as carriers of CEA. Dogs homozygous for the CEA deletions are referred to as affected with CEA.

Testing for the CEA deletion can be carried out in any sample which contains genomic DNA. For example, a sample of blood, hair, spleen, mucosal scrapings, semen, tissue biopsy, saliva or the like can be obtained. In one embodiment, the biological sample is blood.

The presence or absence of the CEA deletion may be determined using a variety of techniques that are well known in the art. For example, genomic DNA may be amplified for use in testing enzymatically through use of PCR (Saiki et al. Science 239:487-491 (1988)) or other in vitro amplification methods such as the ligase chain reaction (LCR) (Wu and Wallace Genomics 4:560-569 (1989)), strand displacement amplification (SDA) (Walker et al. PNAS USA 89:392-396 (1992)), self-sustained sequence replication (3SR) (Fahy et al. PCR Methods Appl. 1:25-33 (1992)), prior to CEA deletion analysis. Techniques for preparing nucleic acids in a form that is suitable for testing for the CEA deletion are well known in the art.

Detecting the presence or absence of the CEA deletion in DNA can be accomplished by a variety of methods including, but not limited to, polymerase chain reaction (PCR), fluorescent in situ hybridization (FISH), hybridization with allele-specific oligonucleotide probes (Wallace et al. Nucl Acids Res 6:3543-3557 (1978)), including immobilized oligonucleotides (Saiki et al. PNAS USA 86:6230-6234 (1989)) or oligonucleotide arrays (Maskos and Southern Nucl Acids Res 21:2269-2270 (1993)), allele-specific PCR (Newton et al. Nucl Acids Res 17:2503-25 16 (1989)), mismatch-repair detection (MRD) (Faham and Cox Genome Res 5:474-482 (1995)), denaturing-gradient gel electrophoresis (DGGE) (Fisher and Lerman et al. PNAS USA 80:1579-1583 (1983)), single-strand-conformation-polymorphism detection (Orita et al. Genomics 5:874-879 (1983)), chemical (Cotton et al. PNAS USA 85:4397-4401 (1988)) or enzymatic (Youil et al. PNAS USA 92:87-91 (1995)) cleavage of heteroduplex DNA, methods based on allele specific primer extension (Syvanen et al. Genomics 8:684-692 (1990)), genetic bit analysis (GBA) (Nikiforov et al. Nuci Acids Res 22:4167-4175 (1994)), the oligonucleotide-ligation assay (OLA) (Landegren et al. Science 241:1077 (1988)), the allele-specific ligation chain reaction (LCR) (Barrany PNAS USA 88:189-193 (1991)), gap-LCR (Abravaya et al. Nucl Acids Res 23:675-682 (1995)), and radioactive and/or fluorescent DNA sequencing using standard procedures well known in the art.

In one embodiment, amplification of genomic DNA for testing for the CEA deletion is performed by PCR. For this embodiment, PCR primers and a method of using the primers in amplification reactions are provided such that different combinations of amplification products are observed when DNA is amplified from affected, carrier or normal dogs.

In one embodiment, testing for the deletion is performed by PCR using a set of four primers. The primers are designed such that when the first and the second primers are used to amplify DNA from a normal chromosome 37 allele, a first amplification product is produced spanning the start breakpoint (5' breakpoint) of the CEA deletion. The third and fourth primers are designed such that when they are used to amplify DNA from a normal chromosome 37 allele, a second amplification product is produced spanning the end breakpoint (3' breakpoint) of the CEA deletion. The first and fourth primers are designed to bind to sites present adjacent to the area deleted in the disease chromosome. The second and third primers are designed to bind to sites present within the area deleted in the disease chromosome.

Neither the set of the first and second primers, nor the set of the third and fourth primers, will amplify a product from a chromosome 37 which has the CEA deletion because there is no binding site present for the second or third primers. Amplification using the first primer and the fourth primer will not produce an amplification product from a normal chromosome 37 because it is beyond the technical limitations of the amplification reactions employed herein to amplify and detect the 7.8 kb (undeleted) sequence present on the normal chromosome. However, when the CEA deletion is present, the binding sites for the first and fourth primers are placed in sufficient proximity with each other on the chromosome(s) with the CEA deletion such that a third amplification product is produced. Thus, the third amplification product does not contain any portion of the CEA deletion.

An example of a set of primers is provided wherein the first primer is upstream or 5' of the start breakpoint of the CEA deletion and the second primer is within the CEA deletion but in sufficient proximity to the first primer site so that an amplification product can be produced spanning the start breakpoint of the CEA deletion. The third primer is within the CEA deletion and the fourth primer is downstream or 3' of the end breakpoint of the CEA deletion. The third and the fourth primer are in sufficient proximity such that an amplification product is produced spanning the end breakpoint of the CEA deletion. The first and the fourth primer sites are sufficiently apart so that when the CEA region is not deleted, these two primers will not produce any amplification product.

It will be recognized by those skilled in the art that the primer designations as first, second, third and fourth is arbitrary and is used herein for clarity in reference to the amplification products generated using the particular primer pairs. It will also be recognized that, while particular sequences of PCR primers are provided herein, other PCR primer sequences can be designed by those skilled in the art to detect the presence or absence of the CEA deletion. Further, the primers may be designed to amplify either strand of of chromosome 37 in the region of the CEA deletion.

Amplification reactions can be carried out using all four primers in the same reaction or amplification of each set can be carried out separately. Thus, simultaneous or sequential amplifications of the genomic DNA in separate reactions using the first and second primers, the third and fourth primers, and the first and fourth primers can also be performed. Regardless of whether the amplifications are performed separately or in combination, the combined results of the amplifications using the three aforementioned primer pairs are interpreted as follows:

1) The presence of only the first and second amplification products is indicative of a normal dog.

2) The presence of the first, second and third amplification products is indicative of a carrier dog.

3) The presence of only the third amplification product is indicative of an affected dog.

Thus, by using the combination of primer pairs described herein, the PCR amplification product profile obtained from a biological sample indicates the CEA status of the dog as normal, a carrier or affected.

When PCR primers are used such that the amplification products are of distinct sizes, the amplification products can be analyzed by standard methods such as electrophoretic separation and detection using ethidium bromide and ultra-violet light, or any other suitable detection method. Alternatively, the PCR products can be isolated and sequenced.

The method of the present invention can be carried out for any breed of dog. In general, dogs known to be inflicted by CEA include Rough and Smooth Collies, Border Collies, Australian Shepherds, Lancashire Heelers, and Shetland Sheepdogs.

Also provided in the present invention are kits for detecting the presence of the CEA deletion in a biological sample from a dog or a nucleic acid sample extracted from the biological sample. The kits of the present invention comprise reagents for nucleic acid based detection of the presence of the CEA deletion. In one embodiment, the kits comprise reagents for extraction/preparation of nucleic acid samples, pairs of primers for amplification of regions spanning the start breakpoint and end breakpoint of the CEA deletion and pairs of primers for amplification of a region spanning the region generated by deletion of the CEA region.

By using the tools and method described herein, dogs which are genetically normal, heterozygous for (deletion in one allele), or homozygous for (deletion in both alleles) the mutation primarily responsible for Collie eye anomaly (CEA) can be identified. Upon identification, such dogs can be eliminated from a breeding stock. Alternatively, dogs which are heterozygous for the CEA allele can be mated with genetically normal dogs to ensure the absence in the litter of dogs affected with CEA.

The invention will be further understood by the following examples, which are intended to be illustrative and not restrictive in any way.

EXAMPLE 1

Figure 2:
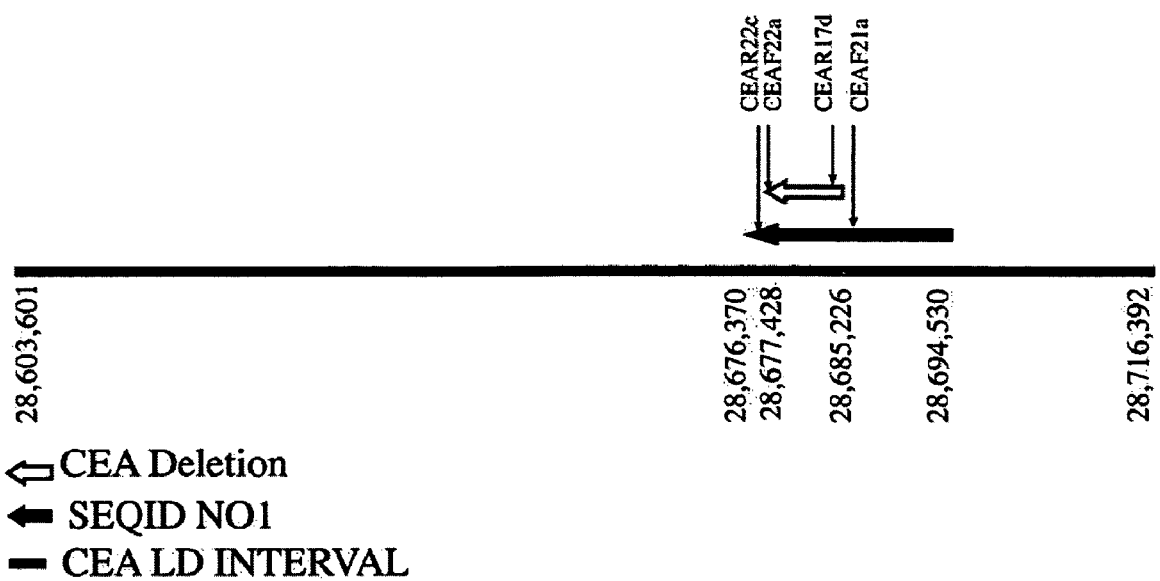
FIG. 2 is a graphical representation of relative positions of the CEA deletion, SEQ ID NO: 1, and primers used to test for the CEA deletion, in relationship to the CEA LD Interval, and in relation to positions in the assembled canine genome sequence (July, 2004 asssembly). Relative to the coordinates of the canine genome sequence, both the sequence of the CEA deletion and of SEQ ID NO:1 are reversed.

This example demonstrates that dogs which are genetically normal, heterozygous for, or homozygous for the mutation primarily responsible for CEA can be distinguished using the method of the present invention. In particular, combinations of four primers are used in PCR reactions to produce amplification products characteristic of dogs that are genetically normal, heterozygous for, or homozygous for the mutation primarily responsible for CEA. The binding positions of the primers relative to SEQ ID NO:1, the CEA deletion and the CEA linkage disequilibrium interval (LD) are provided in FIG. 2.

FIG. 3A provides the nucleotide sequence (SEQ ID NO:10) corresponding to one strand of the amplification product obtained using primer CEAF21a and primer CEAR17d. FIG. 3B provides the nucleotide sequence (SEQ ID NO:11) of the reverse complement of SEQ ID NO:10. In the reverse complement, the boxed pair of nucleotides "GC" flank the start breakpoint of the CEA deletion. That is, on the reverse strand of CFA (Canis familias) chromosome 37 the G is not deleted, but the C is the first deleted nucleotide in the mutant allele. Table 3 provides additional information about the relative binding positions of primers CEAF21 a and CEAR17d.

TABLE 3

| Primer | CEAF21a | CEAR17d |
|---|---|---|
| Sequence | GGAGGAGTCATCATGACTTGC (SEQ ID NO:2) | GACTGGTATTATCAAAGGTCAC (SEQ ID NO:4) |
| Reverse Complement of Sequence | GCAAGTCATGATGACTCCTCC (SEQ ID NO:3) | GTGACCTTTGATAATACCAGTC (SEQ ID NO:5) |
| Binding site sequence, in SEQ ID NO:1 | GGAGGAGTCATCATGACTTGC (SEQ ID NO:2) | gtgacctttgataataccagtc (SEQ ID NO:5) |
| Location relative to SEQ ID NO:1 | 9213-9233 | 9495-9474 |
| Location relative to START of CEA deletion | −89 to −69 | +194 to +173 |
| Location relative to Assembled Canine Genome Sequence | chr37:28,685,296-28,685,315 | chr37:28,685,033-28,685,054 |

FIG. 4A provides the nucleotide sequence (SEQ ID NO:12) corresponding to one strand of an amplification product obtained using primers CEAF22a and primer CEAR22c. FIG. 4B (SEQ ID NO:13) provides the reverse complement of SEQ ID NO:12. In the reverse complement, the boxed pair of nucleotides "GT" flank the end breakpoint of the CEA deletion. That is, on the reverse strand of CFA 37, the G is the last deleted nucleotide and the T is not deleted in the mutant allele. Table 4 provides additional information about the relative binding sites of primers CEAF22a and CEAR22c.

TABLE 4

| Primer | CEAF22a | CEAR22c |
|---|---|---|
| Sequence (forward) | TGTCCTCCGTACCATCGTGT (SEQ ID NO:6) | CTAGTCTGTCAATAGCACCACTA (SEQ ID NO:8) |
| Reverse Complement of Sequence | ACACGATGGTACGGAGGACA (SEQ ID NO:7) | TAGTGGTGCTATTGACAGACTAG (SEQ ID NO:9) |
| Binding site sequence, in SEQ ID NO:1 | TGTCCTCCGTACCATCGTGT (SEQ ID NO:6) | TAGTGGTGCTATTGACAGACTAG (SEQ ID NO:9) |
| Location relative to SEQ ID NO:1 | 16739-16758 | 17420-17442 |

TABLE 4-continued

| Primer | CEAF22a | CEAR22c |
|---|---|---|
| Location relative to END of CEA deletion. | -363 to -344 | +341 to +319 |
| Location relative to Assembled Canine Genome sequence | chr37:28,677,770-28,677,789 | chr37:28677088-28677110 |

To distinguish CEA affected, carrier and normal dogs, the primers disclosed in Table 3 and 4 (and which are summarized in Table 5) were used as follows.

TABLE 5

| Primer | Sequence | Binding Site | Location |
|---|---|---|---|
| CEAF21a | GGAGGAGTCATC-ATGACTTGC (SEQ ID NO:2) | GGAGGAGTCATC-ATGACTTGC (SEQ ID NO:2) | 9213-9233 |
| CEAR17d | GACTGGTATTATC-AAAGGTCAC (SEQ ID NO:4) | gtgacctttgata-ataccagt (SEQ ID NO:5) | 9474-9493 |
| CEAF22a | TGTCCTCCGTACC-ATCGTGT (SEQ ID NO:6) | tgtcctccgtac-catcgtgt (SEQ ID NO:6) | 16739-16760 |
| CEAR22c | CTAGTCTGTCAA-TAGCACCACTA (SEQ ID NO:8) | TAGTGGTGCTATT-GACAGACTAG (SEQ ID NO:9) | 17420-17442 |

CEAF21a is a forward primer and designated herein as a first primer, CEAR17d is a reverse primer and is designated herein as a second primer. CEAF22a is a forward primer and is designated herein as a third primer and CEAR22c is a reverse primer and is designated herein as a fourth primer. Three sets of primers for PCR tests as depicted in Table 6 ("PCR Test #" and "Primers" columns) were performed. These sets of primers were used to amplify genomic DNA extracted from canine blood samples by the phenol-chloroform method (Sambrook et al. 1989). In initial studies, DNA was used from 3 selected dogs whose CEA genetic status (affected, normal or carrier; "CEA Status" column) had been previously determined by experimental breeding studies. In subsequent studies, DNA was used on a larger set of samples representing more than 20 dogs of each genotype (affected, normal or carrier), for which the genotype that had been previously established by experimental breeding studies. All amplifications used the same PCR program: 96° C. for 2 minutes; 30 cycles of 96° C. (20 seconds), 58° C. (20 seconds), and 72° C. (40 seconds); and a final extension at 72° C. for 5 minutes. PCR products were analyzed by eletrophoresis through a 1.5% agarose gel (FIG. 5). The assignment of phenotypes was based on the presence or absence of particular size PCR products as listed in the "Expected PCR Product" column. PCR test number 4 used all four primers simultaneously.

TABLE 6

| PCR Test # | Primers | CEA Status | Expected Product |
|---|---|---|---|
| 1 | CEAF22a CEAR22c | Affected Normal Carrier | None 704 bp 704 bp |
| 2 | CEAF21a CEAR22c | Affected Normal Carrier | 430 bp None 430 bp |
| 3 | CEAF21a CEAR17d | Affected Normal Carrier | None 283 bp 283 bp |
| 4 | CEAF22a CEAR17d CEAF21a CEAR22c | Affected Normal Carrier | 430 bp 283 bp 704 bp 283 bp 430 bp 704 bp |

As shown in Table 6 and FIG. 5, for CEA test 1 (primers CEAF22a and CEAR22c) no product is amplified from affected (A), but a 704 bp product is amplified from both Normal (N) and Carrier (C). This result is obtained because, in the N and C samples, there is at least one copy of the normal CEA allele on which the CEAF22a and CEAR22c primer binding sites are separated by 704 base pairs (bp). However, the CEAF22a binding site lies within the region of DNA that is deleted from both alleles in the affected animals, thus there is no binding site for CEAF22a present on the mutant chromosome and no amplification product can be detected. The sequences of each strand of the 704 bp product generated by PCR using primers CEAF22a and CEAR22c is disclosed in FIGS. 4A and 4B.

As shown in FIG. 5, for CEA test 2 (primers CEAF21a and CEAR22c) a 430 bp product is amplified from both affected (A) and carrier (C), but no product is amplified from Normal (N). This result is obtained because, in both affected and carrier dogs, there is at least one allele with the CEA deletion. The deletion juxtaposes the CEAF21a and CEAR22c primer binding sites such that they are separated by 430 bp on the mutant allele. However, in the normal allele (no PCR product observed), the CEAF21a and CEAR22c primer binding sites are over 7,800 bases apart. Thus, the theoretical product from normal DNA is too large to be amplified and/or observed under the described testing conditions using the CEAF21a and CEAR22c primers. The sequence of one strand of the 430 bp product (SEQ ID NO:14) generated by PCR using primers CEAF21 a and CEAR22c is provided in FIG. 6 wherein the boxed nucleotides "GT" are juxtaposed due to the deletion.

As shown in FIG. 5, for CEA test 3 (primers CEAF21a and CEAR17d), no product is amplified from affected (A), but a 283 bp product is amplified from both Normal (N) and Carrier (C). This result is obtained because, in the N and C samples, there is at least one copy of the normal CEA allele, and the CEAF21a and CEAR17d primer binding sites are separated on the normal allele by 283 bp. However, the CEAR17d binding site lies within the region of DNA that is deleted from both alleles in the affected phenotype, thus there is no binding site for CEAR17d and no amplification product can be detected. The sequence of both strands of the 283 bp product generated by PCR using primers CEAF21a and CEAR17d is disclosed in FIGS. 3A and 3B. Subsequent tests have confirmed that the indicated length of the 283 bp product is correct despite its apparent migration as a longer product in FIG. 5.

In CEA test 4, all primers for tests 1 through 3 are multiplexed, with each of the attendant PCR products produced as when the tests are performed with the single sets 1-3. As can be seen from test 4, only one product (430 bp) is amplified from affected (A), while a 283 bp and a 704 bp product are amplified from Normal (N); and all 3 products (283, 430, and 704 bp) are amplified from the Carrier (C) sample when all four primers are used.

Thus, this Example demonstrates that, by using the method of the present invention, dogs that are normal at the CEA locus, or are heterozygous for, or are homozygous for CEA mutation can be identified.

While this invention has been illustrated by specific embodiments, routine modifications will be apparent to those skilled in the art and such modifications are intended to be within the scope of the invention and the following claims.

The invention claimed is:

1. A method for identifying a dog as normal, heterozygous for, or homozygous for the collie eye anomaly (CEA) mutation comprising the steps of:
    a) obtaining a biological sample comprising DNA from the dog; and
    b) testing the biological sample for a mutation in a region of chromosome 37, wherein the mutation is a deletion of nucleotides 9,302 to 17,101 of SEQ ID NO: 1,
    wherein identification of the deletion in only one allele is indicative of a dog that is heterozygous for the CEA mutation, identification of the deletion in both alleles is indicative of a dog that is homozygous for the CEA mutation and the absence of the deletion in both alleles is indicative of a normal dog.

2. The method of claim 1, wherein the presence or absence of the deletion is tested by amplification of the DNA followed by analysis of the amplification products.

3. The method of claim 2, wherein the amplification is carried out by using a set of four primers,
    wherein, in the absence of the deletion, amplification using the first and the second primers produces a first amplification product spanning the start breakpoint of the deletion, amplification using the third and fourth primers produces a second amplification product spanning the end breakpoint of the deletion, and amplification using the first and the fourth primer does not produce any detectable amplification product; and
    wherein, in the presence of the deletion, amplification using the first and the fourth primer produces a third amplification product which does not contain the deleted region.

4. The method of claim 3, wherein first, second and third amplification products are of different sizes.

5. The method of claim 2, wherein the first primer binds to a sequence upstream of the start breakpoint of the deletion, the fourth primer binds to a sequence downstream of the end breakpoint of the deletion and the second and the third primers bind to sequences within the deleted region.

6. The method of claim 3, wherein the amplification using the first and second primers, the amplification using the third and fourth primers, and the amplification using the first and fourth primers are each performed in separate reactions.

7. The method of claim 3, wherein the amplification using the first and second primers, the amplification using the third and fourth primers, and the amplification using the first and fourth primers are performed in the same reaction.

8. The method of claim 3, wherein the first primer has the sequence of SEQ ID NO:2, the second primer has the sequence of SEQ ID NO:4, the third primer has the sequence of SEQ ID NO:6, and the fourth primer has the sequence of SEQ ID NO:8.

9. The method of claim 3, wherein the first amplification product comprises the sequence of SEQ ID NO:10.

10. The method of claim 3, wherein the the second amplification product comprises the sequence of SEQ ID NO:12.

11. The method of claim 3, wherein the third amplification product comprises the sequence of SEQ ID NO:14.

12. The method of claim 1, wherein the biological sample is selected from the group consisting of blood, hair, mucosal scrapings, semen, tissue biopsy and saliva.

13. The method of claim 12, wherein the biological sample is blood.

14. The method of claim 1, wherein the dog is selected from the group consisting of Rough and Smooth Collies, Border Collies, Australian Shepherds, Lancashire Heelers, and Shetland Sheepdogs.

* * * * *

SEQUENCE LISTING

```
<160> NUMBER OF SEQ ID NOS: 14

<210> SEQ ID NO 1
<211> LENGTH: 18160
<212> TYPE: DNA
<213> ORGANISM: canis familiaris

<400> SEQUENCE: 1
gtgtattcac atcaaccagc ttgtgggctt gtaggtggcc aagggaggtc         50
agatcaggtt gagacaattc cagcgaatgg cctgcccttc cacctaaagc        100
cctgggatct ttccatattt ctgtccttgt ttgttttttg cgctgcccac        150
agtacaaggt aggattgtga agtaggccag ttgctctctc tgtgttcttc        200
tttcctcttc ctgtttattt ttcttaaaga ttttatttat ttatttatga        250
gaggcacaga gagaggcaga gacataggca gaggaacaag caggctcccc        300
atagggaggg actcgatccc aggaccccgg gatcaccacc tgagctgaag        350
gcagatgctc aaccactgag ccacctgggt gccccctctt cctgcctttt        400
tgtcttctct tcatctccac tgcgctgtct tcatgttagc cagagttttc        450
ctttactgtt gaggggagtc tgtttccttg ttacaccccg actccataca        500
actcctgctg tcttttttagg agctgaacaa gcgcctgaca gctccacctg        550
cggcttttct ctgtcatttg gatgatctgc ttcgcccact gttgaaggac        600
actactttcc ccagcgaagc tatgttcacc tgtgatcatg tggccgaggc        650
actgatacta cgggtgcgga gtgaactctc tggtctcccc ttttattgga        700
atttccactg cattcctgct agcccttccc tggtgagtgt aattcaagtg        750
tggagtgggg aaggggaatg ccagctgctt caagatgaat ctttaggtgt        800
tcttattttt gtgtggattc cacttgaaat tcttcttcag tcagaacact        850
ttccttgatt agacagaagg caaaacagat tctcgactgg tacatctttt        900
ccttgcaaag ggagcagggt ttgggtttac ctgctttatt gagcgtcttt        950
aatattcaac atttattaag catcacttta ggctggttgt taggtgtcca       1000
gatctaaaac aaatagccta ttcctggagt ttataatcta gtgagaagat       1050
agacaggaag cagaataaag tatggtaaat tctttggttg aagtaagctc       1100
aggatgagtg aaagtttgaa aaacctttt ttgaagagag ttttttttt       1150 cctttagaaa gtgaggggg aggggaagag ggagagagag agagagagag       1200
```

-continued

| | |
|---|---|
| agaaagagag agagagaatc ccaagcaggc accatgccca acagggagcc | 1250 |
| caacatgggg ctcaatctta caaccctgag atcatgacct gggccgaaat | 1300 |
| caagagttgg gtgtttcacc gactgggcca ctgaggcacc ccattgaaga | 1350 |
| gatagtttct aagttgtgtt ttggagatga ggaggggata accgggagaa | 1400 |
| gatcaggtca gtctaggctg gagtgcattt tgagaggcag ggagatgtat | 1450 |
| aggtatgggg caagggaggg aatttcatga ctgcaggaag ttgtgggaaa | 1500 |
| tgaggtgggc atttttgaaga attctaatga gtttggattt tatccttaag | 1550 |
| gcaacagaga ttcattgaaa aagtttattt tattattaga aaatatttaa | 1600 |
| tttatttatt tgagagagta agagccagag agatcagagg gagagggaca | 1650 |
| gggaaaagca ggcttgctgc tgaacagaga tcccagtgtg gggcttgatc | 1700 |
| tcaggaccct gagtcatgac ctgagctgaa ggcagacgct taaccgactg | 1750 |
| agccacccag gtgcctgcat tgaaaaactt taagcagggg tttaacatga | 1800 |
| tccagttcag atcagtctgg caaaggatag agtacgtgcc agtgttagct | 1850 |
| acctttctga acatttgtca ttggatcctc atgactatcc tgcaagataa | 1900 |
| gtagtattta ttccttgttt tcagagtagg aagccaagat tgaaggcaat | 1950 |
| gtgtccaaag tcatctaact tgtaagtgaa tgagctggaa ttttactccc | 2000 |
| agggaggtct gattcgagag cctatttca aggactagga tgataatgtc | 2050 |
| ttctgcttac acagctttct aggcttccag agcttttatt ttttatttt | 2100 |
| ttaaagattt atttatttag ttatgataga cacacacaca cacacacaca | 2150 |
| cacacacaca cacacacaca cacagaagca gagacacagg cagagggaga | 2200 |
| agcaggctcc atgctgaaag cccgatgtgg gactcgatcc caggactcca | 2250 |
| ggatcgtgcc ccgggccaaa gacaggcgcc aaaccgctga gccacccagg | 2300 |
| gatccctccc agagctttta ttagaaatta gtttgacatg ggagacacct | 2350 |
| aactctggga aaggggtagt ggaaaggag gtgggtgggg ggttggggtg | 2400 |
| actgggtgac gggcactgag gagggcactt ggcaggatga gcactgggtg | 2450 |
| ttatgctaaa tgttgacaag ttgaactcca ataaaaaaaa ttaaaaaaaa | 2500 |
| ttagtttgag agagacgctg gggtgactca gtggttgagc atctcccttc | 2550 |
| agctcaggtc atgatcctgg ggtcctggga tcgagtccca cattggcttc | 2600 |
| cccacaggga gcctgtttct ccctctgcct gtgtctctgc cttctctgt | 2650 |
| gtctctcata aataaatgag taaaatcttt aaaaaaataa attagtttga | 2700 |
| gagtaaacag taagaacttg tttgcaagaa ttactgccac tggtcccttc | 2750 |
| caccctttta tataaacaga gctgtttcag tcagtagcat tagaggccaa | 2800 |
| ggtcttctat gggaggccta agggtgtagg tttatcagca gaagcacttg | 2850 |
| aagacaagtg ggcatcattt cctatatcct ttctttagtt ttcctgaggt | 2900 |
| catgtgatct tttggcacca acggagtgga tgggaccaag tattttgag | 2950 |
| aaactgttct ttggtggatt tcttttctta agatttattt attatttga | 3000 |
| gagagagaga gtgtgtgtgt gtgtggttgg gagggacagg gcgagggaga | 3050 |
| gagagtctca agcgactcca cgttgagcac cgagcccaat gcgggcttg | 3100 |
| atgccatgac ccttaactga aaccaagagt cagaggctca actgactgta | 3150 |
| ccacccaggt gccctctgg tggagttttg atttggaatc cagtaaaggt | 3200 |

```
ggacttgagt gcttggagaa cttctcattc atctctgaat ttctgaggtc       3250
catcaacagt gtttagcaga taatagtttt gatctgttga ttttcgtgaa       3300
atttttttgt gcaattttcc atcctttaga tagtttacct ctggttcaaa       3350
tccctgtaat ttttttctaa gtaacaccag ggggcactgt tccctcaata       3400
atgcttgttc tggaaccaaa aaaaaaaaaa aaaaaaaaag tgttccggga       3450
gcccttggga agtcctagca atagctagtc tcattgtgca tcacacagcc       3500
ctcgaaattc agaatagtga gattgagaag gtagttctag gagggtgatg       3550
ggctctgata gttttttcc ccccaaatta aaggaaact tgtataatga         3600
tattatacta gaaataata tgtaaaggga aaacgagcta ttctaggcaa        3650
attcctctaa ttgggcagcc ccaataagaa aagaagcttc agtattgggg      3700
agaccattga acaattggtg aacaattagg ctttaaggta aaataaaata       3750
tgtattatta taaaaagaa gactaccagc ccagggaaac ccctgagcct        3800
gaggaagctt tatagggaaa aagttagagc cagcggacac tgtcaaggat       3850
gtaggcggat actattccag gcttgtgtgt gtgtctgtga ggtcacacag       3900
tcataatttt tgtttattac tcattcttgt gatagttttt atttcatttt       3950
ttttcaatga gtaattcatg caaaaggcaa acatttcaaa tagcattaag       4000
aaagggtcta gagtgaaaaa ataggtcctt ctactccacc ctctagtctg       4050
ttattttcct tctttaaagc aactactgat accatcttct tgtgacttct       4100
taaggaaagc tatacgtagg tttgtgtaga tgtaagtatg tgtgtactca       4150
cacaatcaaa tacttatctg ggcgtatgga tgccttttca caaatggcag      4200
catactatcc acactattca gtagcttgct cttttcactt aattatagaa       4250
cttagaaaat atttgtaaca atctgcttgg acaatctgct ttaatattct       4300
ttaatggtaa catagagttt tatttgatgg catatatcaa cttgtattga       4350
atcgatacac tactagtaga tacttaagtt gtttccattc ttttgctgtt      4400
acacatagtg gctactcttg tatttacttt tcctacgtgt aaatgtaaga       4450
gtaactttct agcaatggaa tagttgaatc aaggagtatt tgggggctcc      4500
tggatggctc ggtcggaagg gcgtgcaact cttgatctca gggtcgtgag       4550
tctgagcccc acatcaggtg tagagattgc tcaaaaaaat aaataaacaa       4600
atgtaaaaaa aaggagtatt tgtatcatta atattgctca caataatgcc      4650
agattgtctc tcagagagct tgcacaccta aactcctact agccatgcag      4700
gagagtaaga gaatacagcg tgtggtgtgt tcacgccaag atctcaaggc      4750
tgtgcaggat atcatgaaat atctcaagcc tcagatttct gctttctagc      4800
ccatttccac ttccagccag cttccttcat tccttcttcc tcctcaaaaa      4850
tgaaggagtc caagtatgtg ctcgcaatga cttatccaag gtaatagaaa      4900
tcgagtggtg gagctgagtt acaaaagcat gtgtgttctt cctgccacac      4950
aaaaaacccg ttgtattacc ttggataagt cattgaattt ttatgagact      5000
tggcttcatc attgataaag aggaggcacc agtcccaacc ttactatgga      5050
atcctgggga ctaaatacga gaacatacat agtagtactt agcttcagca      5100
ttactgtgga cctttgagaa cacatactcg gactccctaa ttttccttg       5150
```

-continued

| | |
|---|---|
| aagaaaataa gggccgtgag agtgcttggg attaagccat tttcacatct | 5200 |
| agatgctctc agagccaggg ctagaatcca gatggaattt ccagtctgtt | 5250 |
| gctcttgtca ccatatccaa acctgatagg attcattttg ggattgataa | 5300 |
| ctgccattca gctctcctgc ctctgactgt caacatttca atgggaaatc | 5350 |
| tgcagatgtc aggggtgggg gtgggggtgg gagggtgtta taaatagatt | 5400 |
| tcctctggaa aagattgaca actcctgctt ctgtatctac cacacttcct | 5450 |
| gacctcctta actctcctga gaaatttgag agcagaagcc tcatgggttc | 5500 |
| acagcatgta ctaggcacat agtaggtgtc tgttgaattg gcttgtggaa | 5550 |
| tcgcacctct tcatatatca tcgtctgcaa acgaaggggt gggggtcttc | 5600 |
| ctgacctgaa gtgcttcaag attttttcctt gaaaatcctt gaagtatctg | 5650 |
| tggatttgct ttgaaatcta ttacttcagc cacatgactt gtcctaatta | 5700 |
| attgtcctaa gcatgcatct aacttggaaa tgagttatac cccaatgatt | 5750 |
| cagagtggtg tagtccaatt ctatgaaatt atttgaaaag ttgagatatt | 5800 |
| tactgagaaa aagctaaatt attttttctt tgttgctata tagacattgg | 5850 |
| cgtctggtac atagcttcgg gtgcctggca tggcattact ttatttattt | 5900 |
| atttatttat ttatttattt atttatttat tattattttt aatgatagtc | 5950 |
| atcacagaga gagagagaga gagagagagg cagagacaca ggcagaggga | 6000 |
| gaagcaggct ccatgcaccg gggagcccga cgtgggactc gaccccgggt | 6050 |
| ctccaggatc gcgccctggg ccaaaggcag gcgttaaacc tctgcgccac | 6100 |
| ccagggatcc ctaccctata tatttagata cagcattgat taaaagctgt | 6150 |
| ttctccttat gtttcctgtt tatttaccac cactcaaaga gatcgctgtt | 6200 |
| aaggtggatt cccagagaga ggctggttgt cacctttagg agtttctgtt | 6250 |
| atttgagggc tgccgccaga gggatggtga tgctgcttgg ttaccaattg | 6300 |
| caattacttt cagttcagcc cctctaaaca cggacttgct ttcatacaag | 6350 |
| gattcaccta ttttttccact attcacctcg aacaggacaa aacctaacaa | 6400 |
| aatagttcct aggaaagaag gttgggtctg gagcagatga atttcccccaa | 6450 |
| agcagaactt ctgctgcatt ttgaacagta tttggaggct tcagtttatc | 6500 |
| cttaggacct gaactgggaa ccaggaccag gttgggatgt gctgcatgat | 6550 |
| gggaagaagt gactggtgtt tccagctcca tttgacttct ggccttctgc | 6600 |
| tctgcatcag ccccccctgca tttattgggt cctggtggtg gtacaaaagc | 6650 |
| tgctgcctct cgcccgtatc cccctcaccc caatctcttc tcttctgatc | 6700 |
| tgtccttaga gaagcgtagg ggtgcctata atatggccag ttggccaact | 6750 |
| ctggcttgct gcctattttt ctgaagttat gttggaaacc cactaccctc | 6800 |
| atttattaca tgttgtctat gggcattttc atgaagtaac agcagagttg | 6850 |
| agtattgtga caggggctgt attggctgta gagctgaaaa tattgactat | 6900 |
| ctgacccatg cagaaaatgt tgctgacctc tgatctcggg cctttctttt | 6950 |
| taatgtttcc tttagctcat ctccttgggg aatgtgaagg aaaccttgat | 7000 |
| agcatccttt ggtcacaaag aaattattga ttttattttat ttatttattt | 7050 |
| ttaaaagatt gtatttattt atttatttat ttatttattt atttatttat | 7100 |
| ttatttgaca cagagagaga gtacatgcac aagtaggcag agcggcaagc | 7150 |

```
agaggagaga gggagaagca ggctccctgc tgagtagaga gcccagtacg      7200
ggatcatgac tctctgagcc aaaggcaaag acagactctt aactgactga      7250
gccacacagg tgctccgaga tgattgatta tagttatttt ctttggctaa      7300
ggctcttttc tttctaagac tactggatac cttgtgtagg tgaattaggt      7350
aattattcta tataggtata tgttgttata tgagaacagc atcctagttg      7400
cacagcagca tggctatgct tatgtccttc ttaccttgtt aagagcaagg      7450
tgtgctgggc cagtttcatc cttcctaggc tgacctcttg gtgactggct      7500
ggcttctgtt ccgatgacct tagactttgc tgcatttgtg ggagcagatc      7550
gaaactctca ttctggacta tcatcagccc tgaaatggct tgtaagcagt      7600
ggctgggtct aatttccaag gctttctgct ctctgttgac ttttgtcttc      7650
tgttatgtgc cagctagcac actcttttaa ctacacctac tttcctgaag      7700
cctacttgga ttttctgctt tgttagtct ctgcaggaga gttggaacaa       7750
cacctttctc ttatcaactc tgttacaacc ttctcttaa atcaccactc       7800 tgggctgtct atccatgtgt tctcctctct tcttcccacc cttttatcta      7850
tgctacaaag aaagccctcg aacttctttc atacctat ttagttactg        7900 tattttata gccatgtaaa tggattgctt gcttatgaaa ctgtaagtcc       7950
ctgtgaaaac atatatttt cagtattttt ctagttccta atatagtgtt       8000
cgggagtact ctgtaactgt ctgttggctg attgatatct cttccatgaa      8050
aggtctccca gcatttggtt cgtcctctca tgggcatgag tctggccttg      8100
cagtgccaag tgagggaact agcaaccttg cttcgcatga aagatctaga      8150
gatccaggac taccaggaga gtggggctgt gctgagtcga ggtgagggg       8200 cattcttgg gggtgttggg tggggactgg tacaggtggc caaagggcct       8250
cagaaaatgg gagagtcatt tgcattagag gtgtgcttcc ctgaggaggt      8300
gctgggtact gaccataact ggagacttga ggctgggtga tacttctctc      8350
tgccttgatg acccagctgg catccaagta gccaaaagaa actgtagctg      8400
agtccagcca ttgccccagg caatggcaag gaaagagttt ggaaaggggc      8450
caacagttgt gcaaaactgt acgagggcag cacaaacata gggtgggacc      8500
ctatgaagca tagctccagc ttcagaataa aaattcagtt cgaccttcgt      8550
ctttgtggcg ggatgaactc ctagagcaca tgctgccact gaacacatcc      8600
tgtgttgcta atcaccctct cctcctcctc tgtttgctca cacactcatc      8650
ccttctccca ctggactccg ggtgttacat gtttatgctc cctaccaaga      8700
aatcttgggc tctgtttctt ttccttctca caggcagaaa gctcatctta      8750
agactaacat ttctttctg tattattaca gatcggttga agacggagcc       8800
atttgaagaa aattccttct tggaacaatt tatggtagag gtagagtata      8850
caacaataag gattttcttt ctccttgtgc acttttgctt tattttcttt      8900
ccaggtgccc gagtagtgac ttgtgttttg ggtgctagct ggtttgcatg      8950
gttggagaat ccttctctg caaaagttgc ctatagaaaa tctgttaaaa       9000
cttgagatgc atgtggggaa gatgggtga ataggggc aagactatga        9050 aaggcaaaag tgggctggtg aacatttgta aaaacatctg tgctaacgta      9100
```

| | |
|---|---|
| cctaggagtt tcatttagaa ttccctaacc ttggagagtt tggttgccca | 9150 |
| gtcgatcaaa ttttgcttg ttgagatctg atcacaggtc tggattgtgg | 9200 |
| agcagggtgg ggggaggagt catcatgact tgcccctcca acatcccaca | 9250 |
| gcagaggaag gtgaaaagca cagggttacc atttgggaac tgtcttgtgg | 9300 |
| gcacagtaat ctgtggaaaa tcacagtgtt tatacaaggg gactggcaaa | 9350 |
| ggaatgaatg gggagtagat aattgtggcc tgtcagaagc tcctgcctag | 9400 |
| gtttctcttc taaggattga gcttggccaa agaaacatc tattaaacgg | 9450 |
| caaacagggg agtattaata atagtgacct ttgataatac cagtcaatat | 9500 |
| tgattttctc ctctcactct tttaggactt gttggttgta cagttagtac | 9550 |
| cttcatctta ttgccctctt ttctaattat acacattaac caagctggta | 9600 |
| ctttactatg taagcaaata atgctattat aatattgtgt tctgtataga | 9650 |
| ttactcgtgt ttctgtcttg tcatctaggc tactttgtaa actcctggtg | 9700 |
| gacagggact atgactcata tttcttttga acatgaagtt agtattttc | 9750 |
| gcagggctag gcagaaagca ggtgttttg acttggaacc ttctgttctg | 9800 |
| cctctgtgca gtggctgagc aaagacgcca tcgtgcttgg ggtcttaaca | 9850 |
| gtgagaacca aaaatgcaag ttgagtgctc aagcctatct cctgaagcaa | 9900 |
| tctaactctg gagaagaagg aaagcatgca ctgtgaagtc ctgaggcaga | 9950 |
| gtagatttca gtcttttatg gggaaagaga gcccctaca cctggacttg | 10000 |
| cacagagatt tcctaggcca ttttctgtc ggagagcttc ctccgtctct | 10050 |
| aagtgtaggt tttaaggagg ttaatgcagg ctgaggatga tatgctgatt | 10100 |
| ccctgtctct gccccttagt taaataatac aagacttatt ctcagcccag | 10150 |
| cagagaggtc ccttcctgat ctggtgcctg cgtacctatc cagctgggtt | 10200 |
| tcttgagatt tttcttata aaccttaggc ttcagtcaga gaatggcttt | 10250 |
| gaattgccaa aatgccttcc tctcgccttt atgtcttggc acacattgtt | 10300 |
| tcctttatct ataatgccca atgccctggc cttatctacc ttgtaaactt | 10350 |
| ctattaatct tttaagtgtc agcttttggct tctttgagag acctttccag | 10400 |
| actctccttg taaagataat ccttcttccc tgctgctata gtaccttggt | 10450 |
| tcctacctcc gttttatcac atagaacttt gtgatattac tgtctatagg | 10500 |
| tcttcaagac aatgccttc tcctctgttg atctctgaaa accatctgag | 10550 |
| ggcaaggact gcgttgcatg catttctata tccccggggc ctgaacatag | 10600 |
| tgcctgggag tagtagattc tctgtaagtt tgtgggtgaa gatgttacta | 10650 |
| atttgtgct aggggggagtc tcatgaaaat tggggcagtg tggcctgtgg | 10700 |
| atatggtgct gctgtgagac ctaagtttgg ggtcttcagt tattctcctg | 10750 |
| ctttatttg cagcttgga taaattagta cttccagaga ctctgttttc | 10800 |
| ttatttgcaa aattggaggc tcacctcttc catgcttttg gggtaggggc | 10850 |
| aaccctgcag agtcgaatga gaaagcatag aatcctggtg ccagcccggg | 10900 |
| gaagagtatt actgcattgg aaccaattac caattacttc agaaatactg | 10950 |
| gtctcttaag tcctgggtgg atcacaccca aaccacatag acgtacagaa | 11000 |
| ttttacatat ctgcagagga tctgagagac aagtagctat agctttccat | 11050 |
| ttcacagact aagaaattgg gcctcagaga ggttaagtga cttacctaag | 11100 |

| | |
|---|---|
| gtcatgtcgc tgtagctgta tgtttagagc cttcctacat ttcttgtctg | 11150 |
| ggatcatctc tattttgttt tgccactcta actggttgta cacaccaatt | 11200 |
| aaaggatggt taagggctag gatcatgggg aattattgtg acctctggga | 11250 |
| tcactgcatc gtcctctggg atcaccaaat gttctgcata gctgctagaa | 11300 |
| cccattttct aatgggactg cagaattcct tatggccatt gcatcttttc | 11350 |
| agttactctg cttgtctggg gtcctacaaa caggacacag aagggtcatg | 11400 |
| gggtcaccta aaacagctga aaggatgtgc catcaaaata agcaacatag | 11450 |
| gaagataaac aaaccaggga cagagagctc ggggtgaagg tgcagggggg | 11500 |
| ccagggctga tgtcagaggg ccacgcggtc agtgcctggg gtctgttttt | 11550 |
| cctggttcta ggcgagaggc tggagagata gggcacagag ggcagtagga | 11600 |
| cagggaggtt tctaggatac taaggccagg aaaaatattt aagggttgaa | 11650 |
| cagaggttac atcttcatat ttagttcttt tgttttttcct ccctaccccc | 11700 |
| ccgctttgag ccttggattt ctcatttcca gggagcccaa gggggccagt | 11750 |
| tgatggtggc ccgactggag ggggagtgct ggcagtgttc ttcaagtcga | 11800 |
| ctggacgggg tggcttcagg catgattttc atagagggaa gatcctcgta | 11850 |
| gagagcatct cctaggactg ggagctggga ggcaccgtta ggagtaggag | 11900 |
| atgagtcaac gaatcaggga ccattactgc aaggcagtag gaaccgtgtg | 11950 |
| aaagaagttt aggaggatca ggctggcatg gccttctctc actctggtcc | 12000 |
| actggaggga gttccttctc ccggcccat ccatgcctcc tcctctccat | 12050 |
| ctggttgcca tcaggctgtg tggctgctgg cgggctcttt atttatttat | 12100 |
| cccagtgtaa tggggtgagg agggagctgg cctgaggctg gcattccgag | 12150 |
| gccatgccac tgagccacag gcggtttgca tgggtgtgtg agtcactggg | 12200 |
| gctgcatgct gctcaaacca gacgcggcca ggctcaggga cagcaggcag | 12250 |
| cccaaaatag agccccgccc tctgcagctg gcaacccctg gccaggaatc | 12300 |
| agcccttgac accaaaaacct gagcaattgc atgaagttgg cttcttttcag | 12350 |
| tgagggtggg ggtgggggggg gcacttgaca gagagatcct ctccttccct | 12400 |
| gtcttcagag gagtgtattc agcacaatag tccttcccac tgatgcatgc | 12450 |
| cttatacgat ttaaattaat ctgttcaatc caataccttc agcagtttct | 12500 |
| atcatatact tatatgacta tagtgacatt gatttgactc agcatcctaa | 12550 |
| atgtagccac agcctttgtg tcctgtctag ttttagtact gtcttcattc | 12600 |
| cctgtctggt tgcagcctgt tgctagagca gatgcttcaa gttgtgacga | 12650 |
| tattcattgc tgctcttaga aagctggaag ttatatcaaa gccgccctgg | 12700 |
| gaagaggagg aggagtcctt gaacctggaa attgcttgct gtccagttga | 12750 |
| gttcattcac ggacagcttc tgcttggttt ccttggctgg cgttccattc | 12800 |
| tttacctgct ccttaaatgt tagtgttaat tcaaaattgt gtcctcatcc | 12850 |
| acttgtcctt ctctctctgg gtcatctcat ccagaccca atttgaactg | 12900 |
| tcactattat accaccaagt gccaatttta tatctcccat catgcagccc | 12950 |
| atatttcttt ctgcacattt gatgtttcta cctggatgcg tcccacattg | 13000 |
| tactacccta aacatgtcca aaataagcca cccactcccc ctctttctct | 13050 |

| | |
|---|---|
| tctgatattc ctaatcttgg agaatcctac ccgtatccat tcagctttct | 13100 |
| aagccagaaa cttgggagtt actcactttt ctctttgtcc ttactttcaa | 13150 |
| atcctacttg tcaactatct tttgaatctg ctcctctcta atctggtgtc | 13200 |
| tgttgcctta gaatagcagc acccaccega ctcaccccac aattgaattt | 13250 |
| gtattatgtc agagtgatct ctttgagaca gaaacagaaa tccagttgct | 13300 |
| taaagccatt tagtggttca aactccttgc atggcacaca gggtcgttca | 13350 |
| tgatttggtc ctcttgacct ctacagcttg atcctctgcc actttcccaa | 13400 |
| attgaagtcc tgatgcttat ttattccttg accagtgtgc ctgggattct | 13450 |
| cttctttctt gtcctcacgg cagactcctg ttcagctttc ctgactgcac | 13500 |
| agacatcatc cctttgtga gctttccatg accatttctc ctttccttgg | 13550 |
| tctgttttcc ttgccggcac aggtacactc tcctgctgtt cccgccgcct | 13600 |
| cctgtactga ctgacctctc ccatagcatt tggaggacat ggaacgaaca | 13650 |
| ggatatggga atgaaaagga aggatgggga ggcaaggaaa attgagttgg | 13700 |
| ctgatctttt ctcatttaga ttttccttt agaagacttg ttaattcctt | 13750 |
| ctcctcaatg ttttcttgat atggcttcca tactgcaaca ctctcctgtt | 13800 |
| tttcttccta cttcatcggt tgctcctttt cagaatctcc tgctggttct | 13850 |
| ttctctccct tacctctttt tttttttttt ttaagatttt atttatttat | 13900 |
| tcatgagaga cacagagaga ggcagcgaca caggcagagg gggaagcatc | 13950 |
| tccatgcagg gagcccgatg tgggacccga tcccagtctc caggatcaca | 14000 |
| ccctgagcca aaggcaggca ctcaaccatt gagccaccca ggtgtccccc | 14050 |
| tactttttt taaagtaatc tgtacaccta acgcagggct gaactcacaa | 14100 |
| cgctaacacc ccaagatcaa gaatcgcata ctcctctgac tgagccagcc | 14150 |
| aggtgtctgt cccttacctc ttaatgttgg ggtgcctcag gattcaatca | 14200 |
| ttggtgctct ttttttaactt tagtgatctc atatagtccc atggctttaa | 14250 |
| ctaccacttt attgacaaat cccaaattta atctctaccc ttagacctta | 14300 |
| cctccaaaact ctagactgtc tgcttgatat tcccatgtgg aagtccaaca | 14350 |
| gaatctgaaa ctctacatgt ccaaaactga acttctaacc ttaccccag | 14400 |
| atttgttttt ctaacaacct ccttccatct tagctgatgg aaatgtcacc | 14450 |
| ttttcatttg ctagggccac aaaccttaga gtcatccttg acttctgtct | 14500 |
| ttttctcata tcccacatct agtccatcag gaagtcctgt tggccttcaa | 14550 |
| aacacaccca taatttcacc tttgctgctg ccactctggt ctgagccaca | 14600 |
| attgtctctt tcttgcatca ttgcaataac ctctttattg gtgtctctgc | 14650 |
| tgctacctat gcccccttct ggcccattac cagcaaagtg atcttattaa | 14700 |
| aatacagatc acatcatgat actcccctgc tcaaagtcct tcattagttt | 14750 |
| acattacact tctagagtaa aacctaaagg cctttacagt ggcctacaaa | 14800 |
| gccctacgtg atctggacct cattaccttt ctgatttcat ctaccacttt | 14850 |
| ctccttcctt tactccattg cacccacact ggccgcttgc tgttttttcta | 14900 |
| gcactttcta gcaccacttg cctttagtcc tttatgctgc ccatttcctc | 14950 |
| tgcttggaat gctcttcttt cagatatttg tgtggccaag tccttcactt | 15000 |
| cctttatgtc tggattagtt atctatcgct ttataacaca tcattccaaa | 15050 |

```
atgtcatggt ttaaaacaac aaacagttgt ggaaggtcag gaatttggaa         15100
gcagcttagc tgggtgattc tgattcaggg tctctcatga agtcacagtc         15150
aagatgttgg ctgggaatgt gattattctg aggcactgga gaattcactt         15200
ccaagttctc tcatgtggct gttggcagga gatgctgttg ccctgtaaca         15250
tgacctctcc atggggtttc ttacatgaca tggccctgcc ttcctccaga         15300
gcaagtgatc caaaagacag gcgaagactg aaatggaagc tgcagccttt         15350
ttataaccta atctcaggag tgacagcaca tcactctctt gtggtgatct         15400
cttcattagt agtgaagcag taaatgtagg ccacattcaa ggggagggta         15450
actaagctcc acctcttaag gggaggtgtg tcaaaaatac aatacatggt         15500
tttgttcaaa tgttaccttc acaatggagt ttactgtgag tatcctattt         15550
aaaatcataa gccacatcct cgcctctctg cacatgactc taattttgat         15600
tttttctata gcattcatct tccaacatac tataaaattt ccttatttca         15650
ttatgctcat tgttcatggc atcttccccc tgttagagct tgtaagctga         15700
gcaaggacaa ggatggatgt tttgtgccct ggttcatcca gagtacgtag         15750
aacactgcct ctacacacag taggcactca gtacatattt gttgaatgga         15800
tgaaggaatc ttagcttccc actcttcttt attttcccta tcttatgaat         15850
aggccatgaa atgatcaccc tgttggtagt ctgagaccta gatagccta          15900
ctataaatag atgagtaacc taaggagaga attgctgtca gattgccatt         15950
cattctccca cctgcctgtt tactgggata taatcccaat tttgggatga         16000
actataaacc ttgaatcttt tattactgaa atccctaaa acctctcttt          16050
tagacccagt tcagaaagca actatctggg atccctgggt ggcgcagcgg         16100
tttggcgcct gcctttggcc cagggcgcga tcctggagac ccgggatcga         16150
atcccatatc gggctcccga tgcatggagc ctgcttctcc ctctgcctgt         16200
gtctctgcct ctctctctct ctctgtgact atcataagta aataaataaa         16250
aattaaaaaa aaaaaaaaa aaagaaagca actatctcag aaaccaaaag          16300
aataagaacc taccagggca cctgggtggc tcagtcggtt aagtgtctgc         16350
ctttggctca ggtcatgatc tcagggtcct gggattgagc cccacatcag         16400
gctccctgct caacggggag tctgcttctc tctctccctc tgcccctcc          16450
ccccgtgctt gtgcgggtgc tctttctttc tctctgtctc tctctcaaat         16500
gaataaataa aatcttaaaa aaagaaaaag aacctaccaa aatcctggaa         16550
agaacattag tcatacagcc aaaagcaagt taattagttt cctctttcct         16600
cagttttttcc tctccctgag ctgccctgcc accataagcc cgttattcaa        16650
tatgtagagg aagacacagg actcagcata ggtattttca gtatccccat         16700
gggcatcatg aagcaggata aatctagggg catgagactg tcctccgtac         16750
catcgtgtgt gtcagtactc tgatctagag aaacttacag ttaattcatt         16800
cttccggtag tcagcatggt gcatgttctt gtggggcata cggggatga          16850
taatattatc atcaaagagc tcgctgtgct taatgaatga taatagggc           16900
tacaatagtg tagtgattgg aaaaagcttc ctgcaaaagg caggacttga         16950
tctggacttc tgtgtttgtt tggggttttg ctagggaact aggtggaagg         17000
```

```
                                                              -continued cattttagct gggaagcaca tgggcaaagg atgtaaagtc ataatgagtg          17050
ggtgaggatt agcagaaaat aaggttagca agatgataac tcgaggccag          17100
gttgttgggg agccttaaat gctgggctgg atgattggta ctttattctg          17150
aaggtaaatg tatttcagct ttttttttt ctgccagtaa tccatttatt           17200
tgcctgtttc aatccagtta ttaacatcta tcattacacg cagtgattct          17250
caaacaggca catttcccta ggaaggagat gggcacttcc ttctcgcagt          17300
tattaattac tgttatagat agtgggaagc cgtggaaagt tttggctgga          17350
gaactgacat atgaaagcga tctttggcaa gattaggctg tcagtggtat          17400
gcctatgtga gctgaagaat agtggtgcta ttgacagact aggaaaatca          17450
tgggtggggc tcaattaaat ctaatcttgg gtatacaaag gaatggtttt          17500
ccttatttaa aacacaaatc caccagtatt tgagctctgg aatgaaaatc          17550
tccagggagg aagggatggc tgcatatgtt tctcagctat atttctcggg          17600
aattttgcct cctctttggg gttttctcaa tgtggttcct gtagtcacca          17650
ttgagccctg ctaccagggg tcaccactc ttttctttt ggccccagaa            17700 tatattaaaa ggcttctttc tttatattcc ttttataaaa cgttataggg          17750
gcttatgctt tcaaaagaaa atttataaaa aatctgaggg caaacaaaaa          17800
ggaaatcagg atgaaaattc aaatgggata aaattactga tatccaagag          17850
atggatttct gatgctggga atccttaata gtggagatct tcattaactt          17900
ctgaattctc gtatcctaaa agcctcaaaa tcaagtgttt actaactcaa          17950
atgtctaaag gggacagaca tacaatataa atatgatatc ttatatcagg          18000
ctggatataa tacaacatgt ttttgggggt ctgtggaaaa ctgaatcgca          18050 catgccccc tctatctaga cccaaatagg ttagcacagt tgaacagaca           18100
ctgttctggg ggcttgtgta gtttacttca ctgaaaggaa gtaccagctc          18150
cttctaaaat                                                     18160

<210> SEQ ID NO 2
<211> LENGTH: 21
<212> TYPE: DNA
<213> ORGANISM: artificial sequence
<220> FEATURE:
<223> OTHER INFORMATION: CEAF21a primer

<400> SEQUENCE: 2
ggaggagtca tcatgacttg c                                          21

<210> SEQ ID NO 3
<211> LENGTH: 21
<212> TYPE: DNA
<213> ORGANISM: reverse complement of CEAF21a primer

<400> SEQUENCE: 3
gcaagtcatg atgactcctc c                                          21

<210> SEQ ID NO 4
<211> LENGTH: 22
<212> TYPE: DNA
<213> ORGANISM: artificial sequence
<220> FEATURE:
<223> OTHER INFORMATION: CEAR17d primer

<400> SEQUENCE: 4
```
gactggtatt atcaaaggtc ac                                              22

<210> SEQ ID NO 5
<211> LENGTH: 22
<212> TYPE: DNA
<213> ORGANISM: artificial sequence
<220> FEATURE:
<223> OTHER INFORMATION: reverse complement of CEAR17d primer

<400> SEQUENCE: 5
gtgacctttg ataataccag tc                                              22

<210> SEQ ID NO 6
<211> LENGTH: 20
<212> TYPE: DNA
<213> ORGANISM: artificial sequence
<220> FEATURE:
<223> OTHER INFORMATION: CEAF22a primer

<400> SEQUENCE: 6
tgtcctccgt accatcgtgt                                                 20

<210> SEQ ID NO 7
<211> LENGTH: 20
<212> TYPE: DNA
<213> ORGANISM: artificial sequence
<220> FEATURE:
<223> OTHER INFORMATION: reverse complement of CEAF22a primer

<400> SEQUENCE: 7
acacgatggt acggaggaca                                                 20

<210> SEQ ID NO 8
<211> LENGTH: 23
<212> TYPE: DNA
<213> ORGANISM: artificial sequence
<220> FEATURE:
<223> OTHER INFORMATION: CEAR22c primer

<400> SEQUENCE: 8
ctagtctgtc aatagcacca cta                                             23

<210> SEQ ID NO 9
<211> LENGTH: 23
<212> TYPE: DNA
<213> ORGANISM: artificial sequence
<220> FEATURE:
<223> OTHER INFORMATION: reverse complement of CEAR22c primer

<400> SEQUENCE: 9
tagtggtgct attgacagac tag                                             23

<210> SEQ ID NO 10
<211> LENGTH: 283
<212> TYPE: DNA
<213> ORGANISM: artificial sequence
<220> FEATURE:
<223> OTHER INFORMATION: PCR amplification product

<400> SEQUENCE: 10
gactggtatt atcaaaggtc actattatta atactcccct gtttgccgtt         50
taatagatgt ttcttttggc caagctcaat ccttagaaga gaaacctagg        100
caggagcttc tgacaggcca caattatcta ctccccattc attcctttgc        150

| | |
|---|---|
| cagtcccctt gtataaacac tgtgattttc cacagattac tgtgcccaca | 200 |
| agacagttcc caaatggtaa ccctgtgctt ttcaccttcc tctgctgtgg | 250 |
| gatgttggag gggcaagtca tgatgactcc tcc | 283 |

<210> SEQ ID NO 11
<211> LENGTH: 283
<212> TYPE: DNA
<213> ORGANISM: artificial sequence
<220> FEATURE:
<223> OTHER INFORMATION: PCR amplification product

<400> SEQUENCE: 11

| | |
|---|---|
| ggaggagtca tcatgacttg cccctccaac atcccacagc agaggaaggt | 50 |
| gaaaagcaca gggttaccat ttgggaactg tcttgtgggc acagtaatct | 100 |
| gtggaaaatc acagtgttta caaggggact ggcaaagg aatgaatggg | 150 |
| gagtagataa ttgtggcctg tcagaagctc ctgcctaggt ttctcttcta | 200 |
| aggattgagc ttggccaaaa gaaacatcta ttaaacggca acaggggag | 250 |
| tattaataat agtgaccttt gataatacca gtc | 283 |

<210> SEQ ID NO 12
<211> LENGTH: 702
<212> TYPE: DNA
<213> ORGANISM: artificial sequence
<220> FEATURE:
<223> OTHER INFORMATION: PCR amplification product

<400> SEQUENCE: 12

| | |
|---|---|
| ctagtctgtc aatagcacca ctattcttca gctcacatag gcataccact | 50 |
| gacagcctaa tcttgccaaa gatcgctttc atatgtcagt tctccagcca | 100 |
| aaactttcca cggcttccca ctatctataa cagtaattaa taactgcgag | 150 |
| aaggaagtgc ccatctcctt cctaggaaat gtgcctgttt gagaatcact | 200 |
| gcgtgtaatg atagatgtta ataactggat tgaaacaggc aaataaatgg | 250 |
| attactggca gaaaaaaaa aagctgaaat acatttacct tcagaataaa | 300 |
| gtaccaatca tccagcccag catttaaggc tccccaacaa cctggcctcg | 350 |
| agttatcatc ttgctaacct tatttttctgc taatcctcac ccactcatta | 400 |
| tgactttaca tcctttgccc atgtgcttcc cagctaaaat gccttccacc | 450 |
| tagttcccta gcaaaacccc aaacaaacac agaagtccag atcaagtcct | 500 |
| gcctttgca ggaagctttt tccaatcact cactattgt agccctatt | 550 |
| atcattcatt aagcacagcg agctctttga tgataatatt atcatccccc | 600 |
| gtatgcccac aagaacatgc accatgctga ctaccggaag aatgaattaa | 650 |
| ctgtaagttt ctctagatca gagtactgac acacgatg gtacggagga | 700 |
| ca | 702 |

<210> SEQ ID NO 13
<211> LENGTH: 702
<212> TYPE: DNA
<213> ORGANISM: artificial sequence
<220> FEATURE:
<223> OTHER INFORMATION: PCR amplification product

<400> SEQUENCE: 13

| | |
|---|---|
| tgtcctccgt accatcgtgt gtgtcagtac tctgatctag agaaacttac | 50 |

```
agttaattca ttcttccggt agtcagcatg gtgcatgttc ttgtgggcat           100
acgggggatg ataatattat catcaaagag ctcgctgtgc ttaatgaatg           150
ataatagggg ctacaatagt gtagtgattg gaaaaagctt cctgcaaaag           200
gcaggacttg atctggactt ctgtgtttgt ttggggtttt gctagggaac           250
taggtggaag gcattttagc tgggaagcac atgggcaaag gatgtaaagt           300
cataatgagt gggtgaggat tagcagaaaa taaggttagc aagatgataa           350
ctcgaggcca ggttgttggg gagccttaaa tgctgggctg gatgattggt           400
actttattct gaaggtaaat gtatttcagc tttttttttt tctgccagta           450
atccatttat ttgcctgttt caatccagtt attaacatct atcattacac           500
gcagtgattc tcaaacaggc acatttccta ggaaggagat gggcacttcc           550
ttctcgcagt tattaattac tgttatagat agtgggaagc cgtggaaagt           600
tttggctgga gaactgacat atgaaagcga tctttggcaa gattaggctg           650
tcagtggtat gcctatgtga gctgaagaat agtggtgcta ttgacagact           700
ag                                                               702

<210> SEQ ID NO 14
<211> LENGTH: 430
<212> TYPE: DNA
<213> ORGANISM: artificial sequence
<220> FEATURE:
<223> OTHER INFORMATION: PCT amplification product

<400> SEQUENCE: 14
ggaggagtca tcatgacttg cccctccaac atcccacagc agaggaaggt            50
gaaaagcaca gggttaccat ttgggaactg tcttgtgggt tgttggggag           100
ccttaaatgc tgggctggat gattggtact ttattctgaa ggtaaatgta           150
tttcagcttt ttttttttct gccagtaatc catttatttg cctgtttcaa           200
tccagttatt aacatctatc attacacgca gtgattctca aacaggcaca           250
tttccctagg aaggagatgg gcacttcctt ctcgcagtta ttaattactg           300
ttatagatag tgggaagccg tggaaagttt tggctggaga actgacatat           350
gaaagcgatc tttggcaaga ttaggctgtc agtggtatgc ctatgtgagc           400
tgaagaatag tggtgctatt gacagactag                                 430
```